United States Patent
Beardsley

(10) Patent No.: US 12,064,203 B2
(45) Date of Patent: Aug. 20, 2024

(54) SURGICAL SYSTEMS INCLUDING ADAPTER ASSEMBLIES FOR INTERCONNECTING ELECTROMECHANICAL SURGICAL DEVICES AND END EFFECTORS

(71) Applicant: Covidien LP, Mansfield, MA (US)

(72) Inventor: John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 238 days.

(21) Appl. No.: 17/474,095

(22) Filed: Sep. 14, 2021

(65) Prior Publication Data
US 2021/0401525 A1 Dec. 30, 2021

Related U.S. Application Data

(63) Continuation of application No. 15/797,250, filed on Oct. 30, 2017, now Pat. No. 11,116,594.
(Continued)

(51) Int. Cl.
*A61B 34/00* (2016.01)
*A61B 17/00* (2006.01)
(Continued)

(52) U.S. Cl.
CPC ........ *A61B 34/71* (2016.02); *A61B 17/07207* (2013.01); *A61B 2017/00199* (2013.01);
(Continued)

(58) Field of Classification Search
CPC ......... A61B 34/71; A61B 34/35; A61B 34/76; A61B 17/07207; A61B 17/00234;
(Continued)

(56) References Cited

U.S. PATENT DOCUMENTS 2,777,340 A   1/1957   Hettwer et al.
2,957,353 A   10/1960  Babacz
(Continued)

FOREIGN PATENT DOCUMENTS

CA   2451558 A1   1/2003
CN   1547454 A    11/2004
(Continued)

OTHER PUBLICATIONS

Notification of Transmittal of the International Search Report and the Written Opinion of the International Searching Authority issued in correspondingapplication No. PCT/US2016/027042 dated Jul. 12, 2016.
(Continued)

*Primary Examiner* — Joshua G Kotis
*Assistant Examiner* — Scott A Howell
(74) *Attorney, Agent, or Firm* — Carter, DeLuca & Farrell LLP

(57) ABSTRACT

An adapter assembly for selectively interconnecting an end effector and a surgical device includes a housing configured to connect to the surgical device, a shaft assembly extending from the housing, a cable drive assembly, and a coupling member. The cable drive assembly includes a cable supported in the housing. The coupling member is secured to the cable and configured to connect to the end effector. The coupling member is movable relative to the shaft assembly in response to movement of the cable.

8 Claims, 19 Drawing Sheets

Related U.S. Application Data

(60) Provisional application No. 62/419,031, filed on Nov. 8, 2016.

(51) Int. Cl.
*A61B 17/072* (2006.01)
*A61B 17/29* (2006.01)
*A61B 34/35* (2016.01)

(52) U.S. Cl.
CPC .............. *A61B 17/00234* (2013.01); *A61B 2017/00398* (2013.01); *A61B 2017/0046* (2013.01); *A61B 2017/00473* (2013.01); *A61B 2017/00477* (2013.01); *A61B 2017/0069* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2903* (2013.01); *A61B 2017/2927* (2013.01); *A61B 2017/2929* (2013.01); *A61B 34/35* (2016.02); *A61B 34/76* (2016.02)

(58) Field of Classification Search
CPC .......... A61B 2017/00234; A61B 2017/00199; A61B 2017/00398; A61B 2017/0046; A61B 2017/00473; A61B 2017/00477; A61B 2017/0069; A61B 2017/0034; A61B 2017/07257; A61B 2017/07271; A61B 2017/07278; A61B 2017/07285; A61B 2017/2903; A61B 2017/2927
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,740,699 A | 4/1998 | Ballantyne et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,797,900 A | 8/1998 | Madhani et al. |
| 5,820,009 A | 10/1998 | Melling et al. |
| 5,863,159 A | 1/1999 | Asko |
| 5,865,361 A | 2/1999 | Milliman et al. |
| 5,908,427 A | 6/1999 | McKean et al. |
| 5,954,259 A * | 9/1999 | Viola ............... A61B 17/07207 227/176.1 |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |

(56) References Cited

U.S. PATENT DOCUMENTS

| | | |
|---|---|---|
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,556,151 B2 | 10/2013 | Viola |
| 8,561,871 B2 | 10/2013 | Rajappa et al. |
| 8,561,874 B2 | 10/2013 | Scirica |
| 8,579,921 B2 | 11/2013 | Hathaway |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,852,174 B2 | 10/2014 | Burbank |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |

(56) References Cited

U.S. PATENT DOCUMENTS

| | | |
|---|---|---|
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 11,116,594 B2 | 9/2021 | Beardsley |
| 2001/0031975 A1 | 10/2001 | Whitman |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175960 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0118709 A1 | 5/2011 | Burbank |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0301579 A1 | 12/2011 | Marczyk et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |

(56) References Cited

U.S. PATENT DOCUMENTS

| | | |
|---|---|---|
| 2014/0236174 A1 | 8/2014 | Williams et al. |
| 2014/0249557 A1* | 9/2014 | Koch, Jr. ......... A61B 17/07207 606/170 |
| 2014/0276932 A1 | 9/2014 | Williams et al. |
| 2014/0299647 A1* | 10/2014 | Scirica ............. A61B 17/07207 227/175.1 |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0012014 A1* | 1/2015 | Williams ......... A61B 17/07207 606/143 |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1* | 10/2015 | Nicholas ................ A61B 17/00 606/1 |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0359536 A1* | 12/2015 | Cropper ............... A61B 17/068 227/177.1 |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera |
| 2016/0113648 A1 | 4/2016 | Zergiebel et al. |
| 2016/0113649 A1 | 4/2016 | Zergiebel et al. |
| 2017/0319200 A1 | 11/2017 | Nicholas |
| 2018/0310935 A1 | 11/2018 | Wixey |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2815705 A1 | 12/2014 |
| ES | 2333509 A1 | 2/2010 |
| FR | 2861574 A1 | 5/2005 |
| JP | 2005125075 A | 5/2005 |
| KR | 20120022521 A | 3/2012 |
| WO | 2009039506 A1 | 3/2009 |
| WO | 2011108840 A2 | 9/2011 |
| WO | 2012040984 A1 | 4/2012 |
| WO | 2016025132 A1 | 2/2016 |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 97833 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.

(56) References Cited

OTHER PUBLICATIONS

Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.
U.S. Appl. No. 62/333,584, filed May 9, 2016 to Nicholas.

* cited by examiner

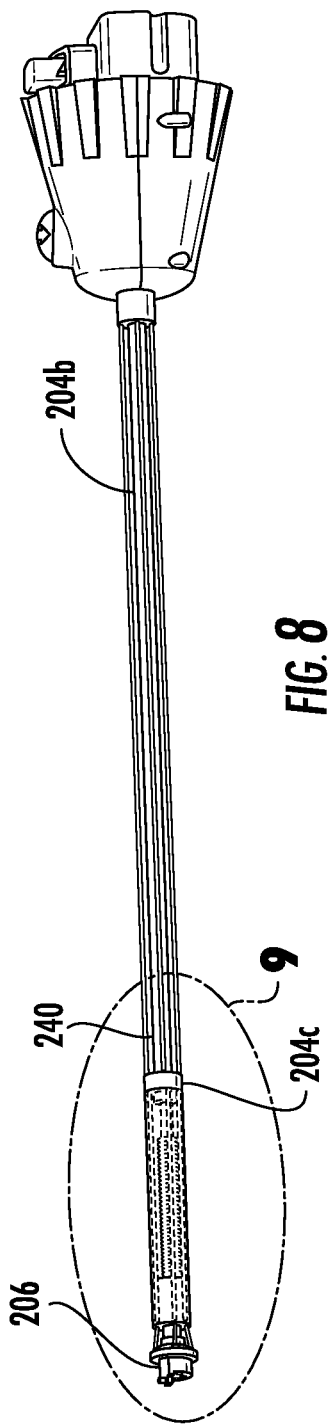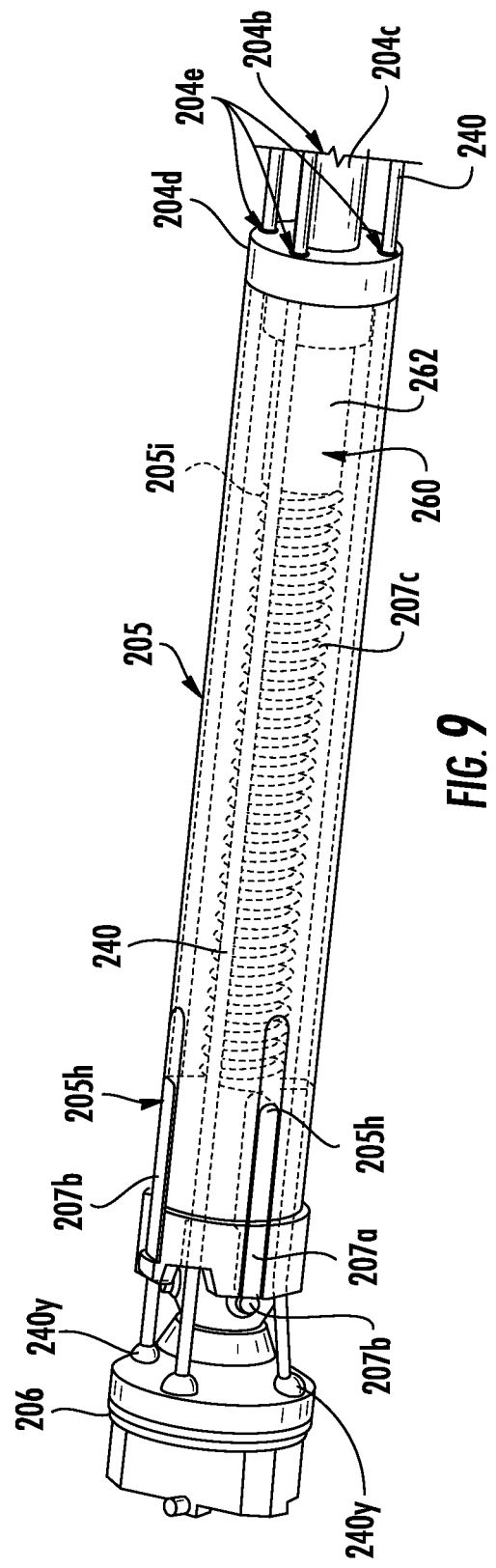
FIG. 8
FIG. 9

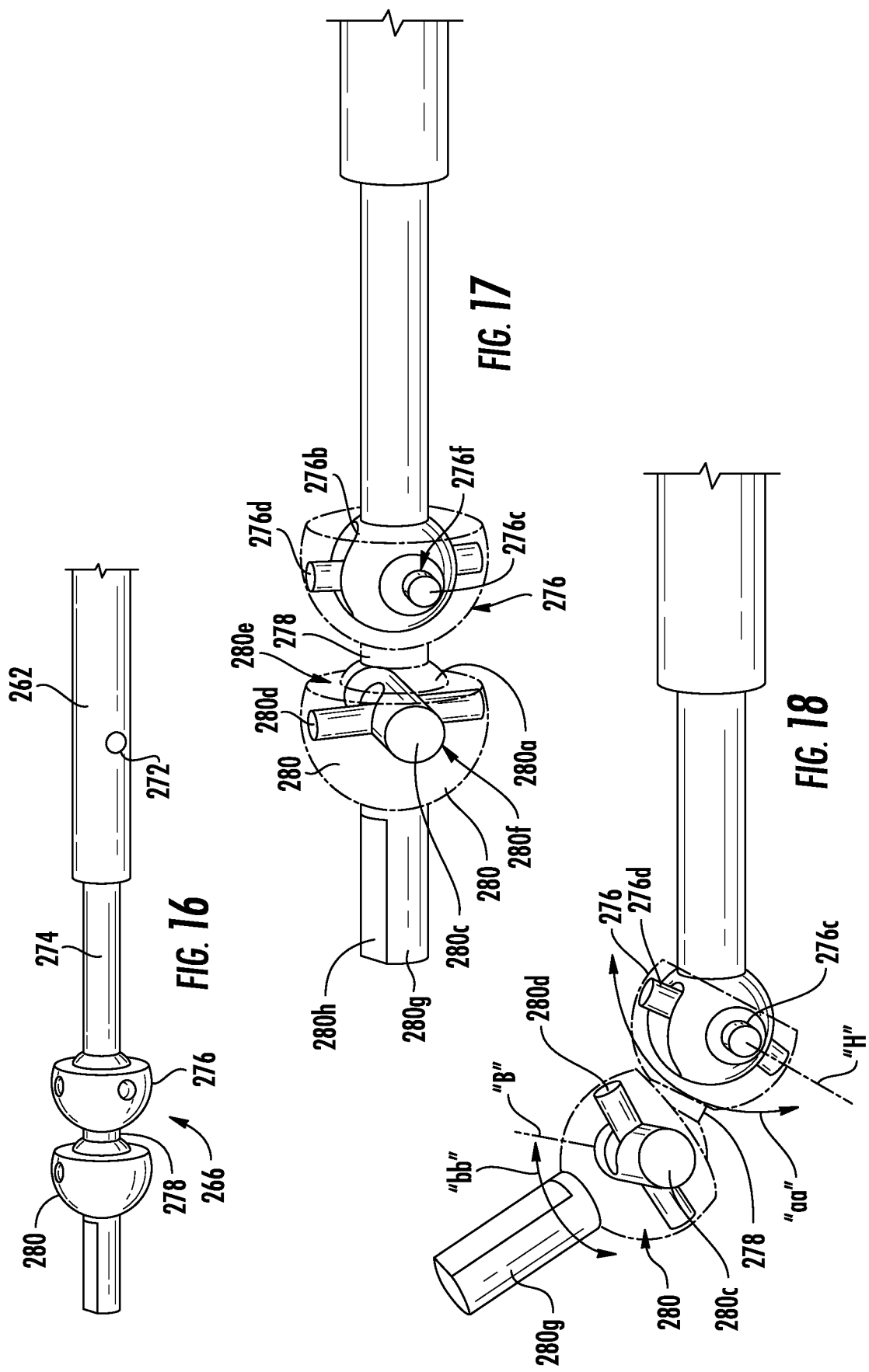

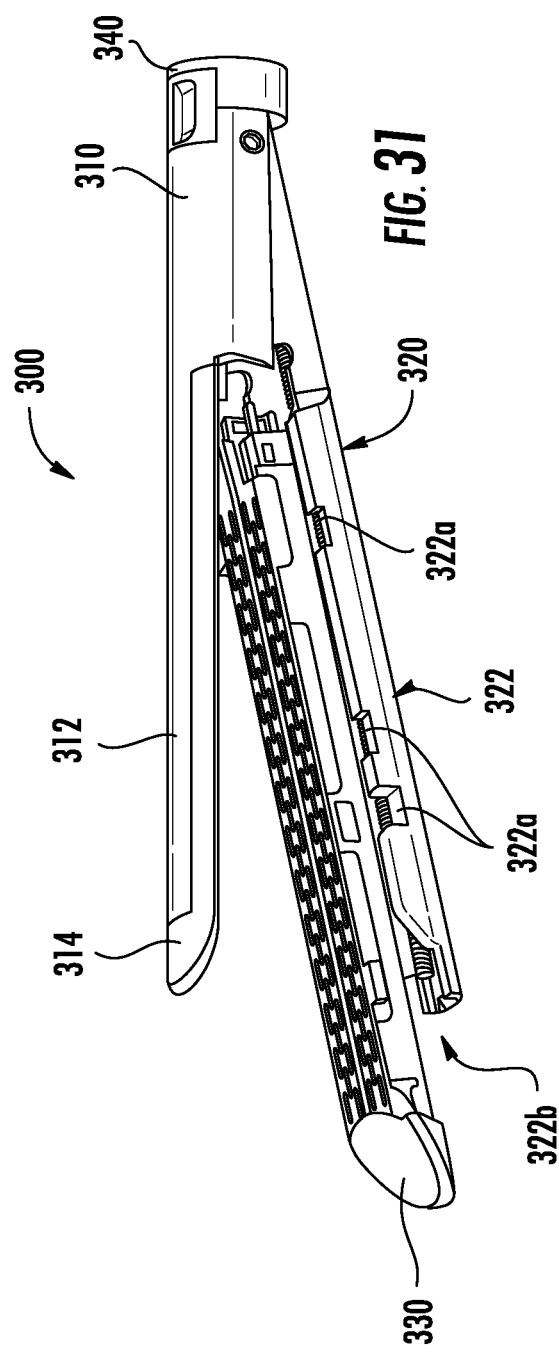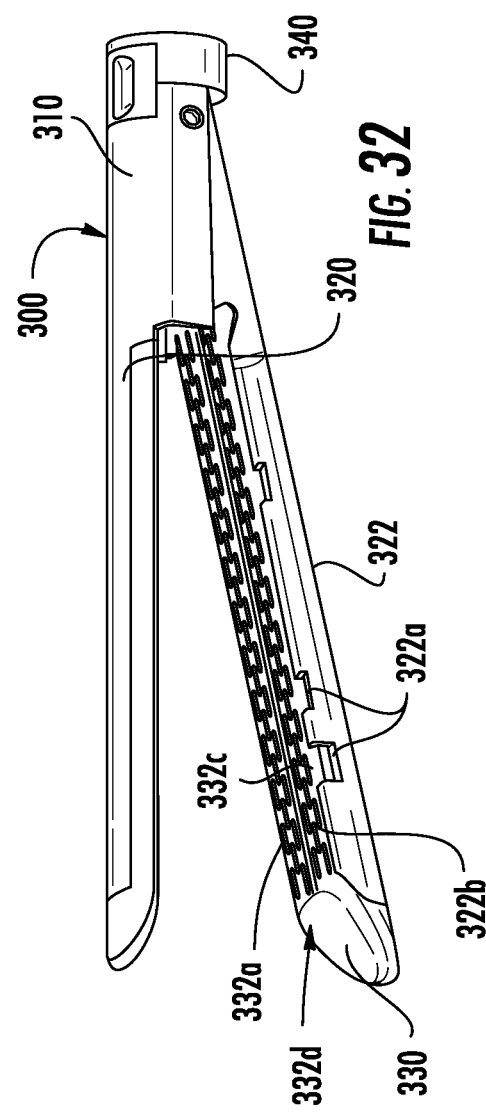

SURGICAL SYSTEMS INCLUDING ADAPTER ASSEMBLIES FOR INTERCONNECTING ELECTROMECHANICAL SURGICAL DEVICES AND END EFFECTORS

CROSS-REFERENCE TO RELATED APPLICATIONS

This application is a continuation of U.S. patent application Ser. No. 15/797,250, filed Oct. 30, 2017, which claims the benefit of U.S. Provisional Patent Application Ser. No. 62/419,031, filed Nov. 8, 2016, the entire disclosure of which is incorporated by reference herein.

TECHNICAL FIELD

The present disclosure generally relates to adapter assemblies for use in surgical systems. More specifically, the present disclosure relates to adapter assemblies to electrically and mechanically interconnect electromechanical surgical devices and surgical end effectors.

BACKGROUND

A number of surgical device manufacturers have developed product lines with proprietary powered drive systems for operating and/or manipulating a surgical device. In many instances the surgical devices include a powered handle assembly, which is reusable, and a disposable end effector or the like that is selectively connected to the powered handle assembly prior to use and then disconnected from the end effector following use in order to be disposed of or in some instances, sterilized for re-use.

Many of the existing end effectors for use with many of the existing powered surgical devices and/or handle assemblies are driven by a linear force. For example, end effectors for performing endo-gastrointestinal anastomosis procedures, end-to-end anastomosis procedures and transverse anastomosis procedures, each typically require a linear driving force in order to be operated. These end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. Many of these adapter and/or adapter assemblies are complex devices including many parts and requiring extensive labor to assemble.

Accordingly, a need exists to develop surgical systems with adapters and/or adapter assemblies that incorporate fewer parts, are less labor intensive to assemble, and are ultimately more economical to manufacture.

SUMMARY

According to an aspect of the present disclosure, an adapter assembly is provided the adapter assembly includes a housing configured to connect to a surgical device, a shaft assembly extending from the housing, a cable drive assembly including a cable supported in the housing, and a coupling member secured to the cable and configured to connect to an end effector. The coupling member is spaced from a distal end of the shaft assembly and movable relative to the shaft assembly in response to movement of the cable.

In some embodiments, the adapter assembly may further include an actuation assembly having a drive shaft connected to a joint assembly. The joint assembly may be coupled to the coupling member and positioned to facilitate articulation of the coupling member relative to the shaft assembly. The joint assembly may include a drive pin rotatably coupled to the coupling member to transfer forces from the drive shaft through the coupling member. The joint assembly may include one or more joints having a universal joint configuration. The one or more joints may include a first joint and a second joint movable relative to the first joint. The joint assembly may include a joint housing that supports the one or more joints therein. The joint housing may extend between the coupling member and the shaft assembly.

In certain embodiments, the adapter assembly may further include a rotation mechanism operatively coupled to the housing. The shaft assembly may define a longitudinal axis. The rotation mechanism may be configured to selectively lock rotational movement of the shaft assembly about the longitudinal axis. The rotation mechanism may include a locking ring coupled to the housing and a locking blade. The locking blade may be engagable with the locking ring to lock rotational movement of the shaft assembly. The locking blade may be movable relative to the locking ring to enable the shaft assembly to rotate about the longitudinal axis.

According to another aspect of the present disclosure, a surgical stapling apparatus is provided. The surgical stapling apparatus includes an end effector having a staple cartridge assembly and an anvil assembly, a surgical device configured to operate the end effector, and an adapter assembly for selectively interconnecting the end effector and the surgical device.

The adapter assembly defines a longitudinal axis and includes one or more cables, a coupling member secured to the one or more cables and selectively connectable to the end effector, and a firing assembly coupled to the coupling member and having a universal joint. The universal joint may be configured to facilitate articulation of the end effector relative to the longitudinal axis and may be rotatable to eject staples from the staple cartridge assembly.

In some embodiments, the one or more cables include a plurality of cables movable to articulate the coupling member in conjunction with corresponding movement of the universal joint.

In certain embodiments, the coupling member may include an input coupler and the firing assembly may include a drive pin. The input coupler may rotatably receive the drive pin therein. The coupling member may further include an output coupler configured to rotate in response to rotation of the input coupler. The end effector may include an input shaft rotatably coupled to the output coupler of the coupling member. The output coupler may be configured to rotate the input shaft to effectuate an approximation of the staple cartridge assembly and the anvil assembly, and ejection of staples from the staple cartridge assembly.

In some embodiments, the end effector includes a coupling ring and a slide member. The slide member may be movable between open and closed positions relative to the coupling ring to selectively couple the end effector to the coupling member of the adapter assembly. The slide member of the end effector may define a locking channel, and the coupling member of the adapter assembly may include a pin. The pin may be receivable within the locking channel to selective lock the coupling member within the coupling ring. The slide member may be spring biased toward the closed position.

In certain embodiments, the one or more cables may include a spherical ferrule that couples the one or more cables to the coupling member. The coupling member may be pivotable about the spherical ferrule.

In some embodiment, the adapter assembly may further include a shaft assembly supported about the firing assembly. The shaft assembly may extend to a crown spaced from the coupling member. The crown may define one or more cable lumens configured to receive the one or more cables therethrough.

According to yet another aspect of the present disclosure, a surgical system is provided. The surgical system includes an end effector, a surgical device configured to operate the end effector, and an adapter assembly for selectively interconnecting the end effector and the surgical device. The adapter assembly defines a longitudinal axis and includes a firing assembly having first and second joints multi-axially supported in a joint housing. The first and second joints may be configured to move in sequence to facilitate articulation of the end effector relative to adapter assembly.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 8 is a perspective view of the adapter assembly shown in FIG. 3 with portions thereof removed or shown in phantom for clarity;

FIG. 9 is an enlarged, perspective view of the indicated area of detail delineated in FIG. 8;

FIGS. 16-18 are progressive views of a distal portion of a firing assembly of the adapter assembly of FIG. 3, illustrating the firing assembly in unarticulated and articulated positions;

FIGS. 30-32 are progressive views illustrating a reload of the end effector of the electromechanical surgical system of FIG. 1 being coupled to the end effector;

DETAILED DESCRIPTION

Figure 1:
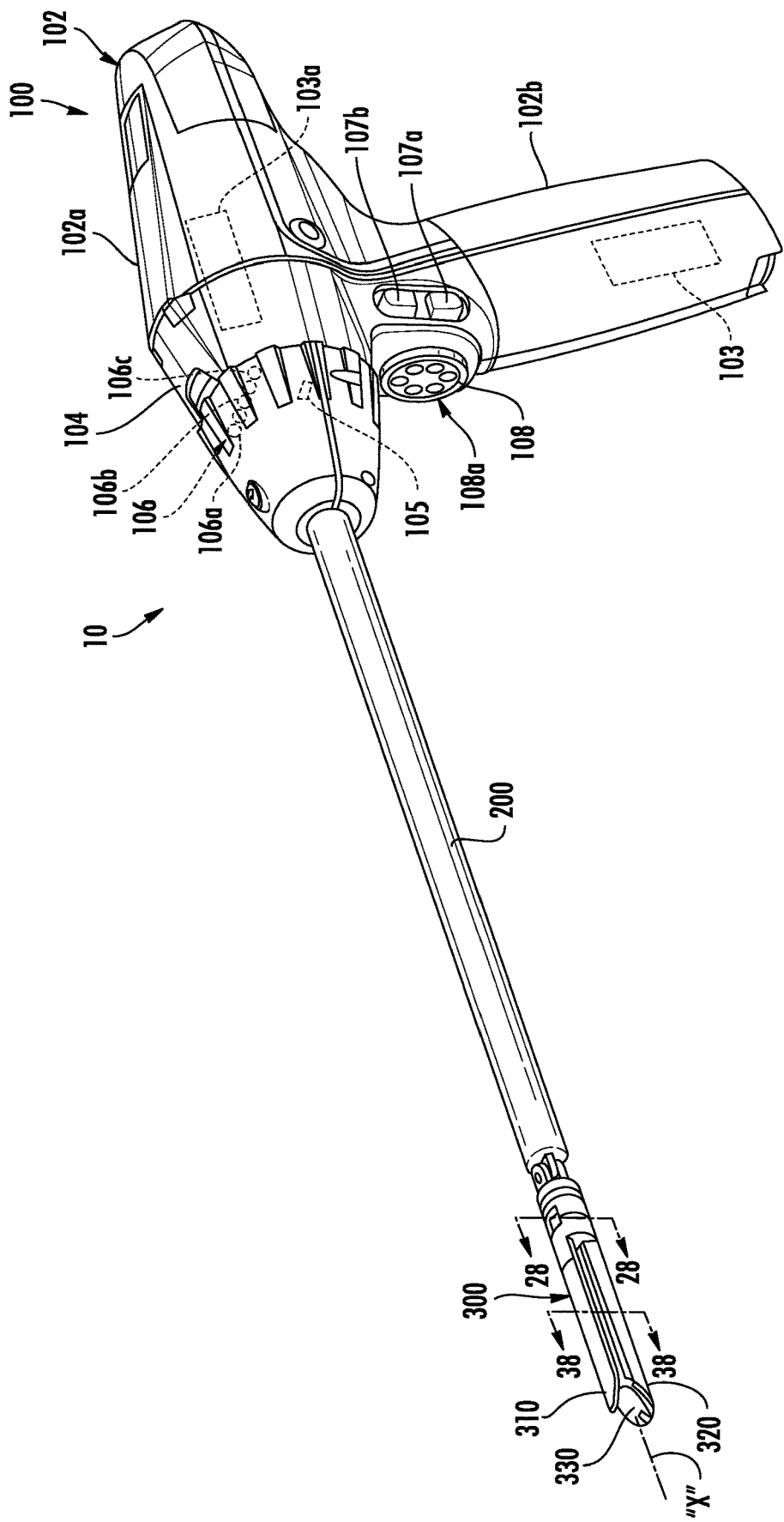
FIG. 1 is a perspective view of an electromechanical surgical system in accordance with the principles of the present disclosure, the electromechanical surgical system having an end effector shown in an unarticulated and clamped position.

Electromechanical surgical systems of the present disclosure include surgical devices in the form of powered handheld electromechanical instruments configured for selective attachment to different end effectors that are each configured for actuation and manipulation by the powered handheld electromechanical surgical instrument. In particular, the presently described electromechanical surgical systems include adapter assemblies that interconnect the powered handheld electromechanical surgical instruments to different end effectors for effectuating actuation and/or manipulation of the different end effectors.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein, the term "distal" refers to that portion of the system, assembly, device, and/or component thereof, farther from the user, while the term "proximal" refers to that portion of the system, assembly, device, and/or component thereof, closer to the user. As used herein, the term "clinician" refers to a doctor, nurse, or other care provider and may include support personnel. In the following description, well-known functions or construction are not described in detail to avoid obscuring the present disclosure in unnecessary detail.

Figure 2:
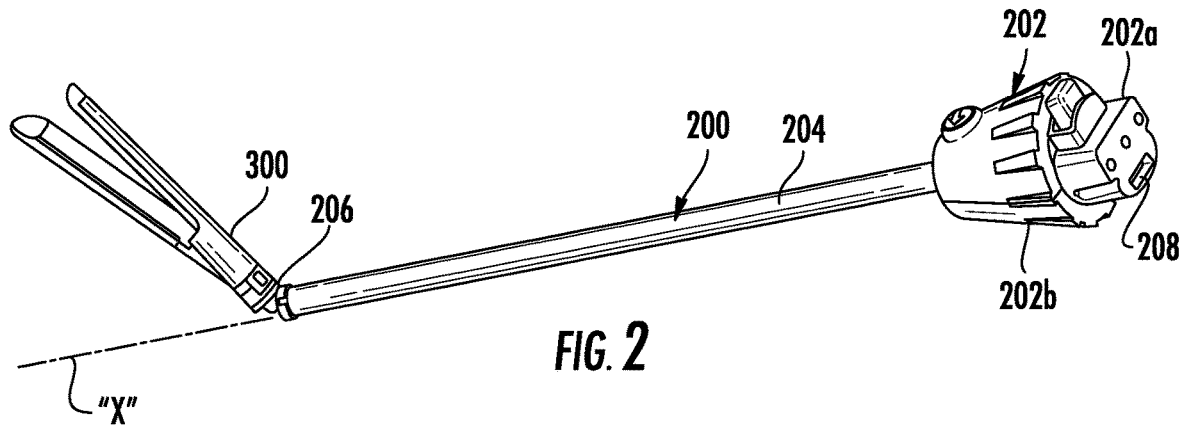
FIG. 2 is a perspective view of an adapter assembly of the electromechanical surgical system of FIG. 1 with an end effector coupled to the adapter assembly and shown in an unclamped and articulated position.
Figure 3:
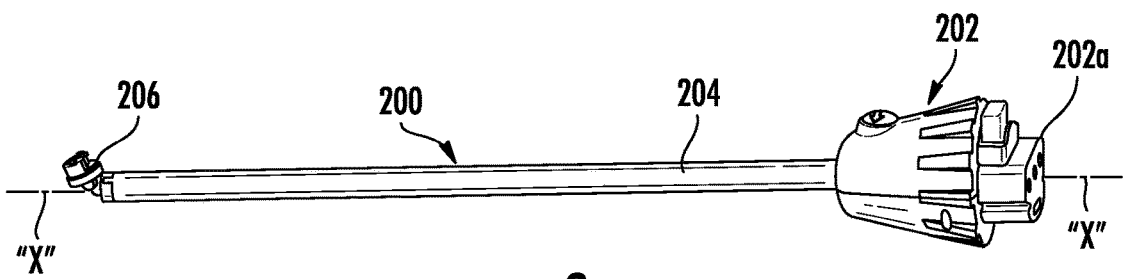
FIG. 3 is a perspective view of the adapter assembly shown in FIG. 2, with the end effector removed therefrom.
Figure 4:
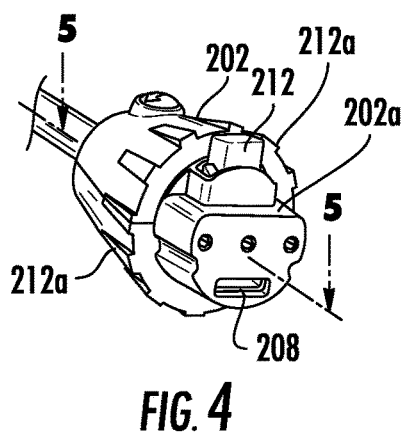
FIG. 4 is an enlarged, perspective view of a proximal portion of the adapter assembly shown in FIG. 3.

Turning now to FIGS. 1 and 2, an electromechanical surgical system, in accordance with the present disclosure, generally referred to as 10, includes a surgical device 100 in the form of a powered handheld electromechanical instrument, an adapter assembly 200, and a surgical loading unit (e.g., multiple- or single-use loading unit) or end effector 300. The surgical device 100 is configured for selective connection with the adapter assembly 200, and, in turn, the adapter assembly 200 is configured for selective connection with the end effector 300. Together, the surgical device 100 and the adapter assembly 200 may cooperate to actuate the end effector 300.

The surgical device 100 of the electromechanical surgical system 10 includes a handle housing 102 that supports a controller or circuit board (not shown) and a drive mechanism 106 situated therein. The circuit board is configured to control various operations of the surgical device 100. The handle housing 102 defines a cavity therein (not shown) for selective removable receipt of a rechargeable battery 103 therein. The battery 103 is configured to supply power to electrical components of the surgical device 100. The drive mechanism 106 within the handle housing 102 is configured to drive rotatable shafts 106a-106c (and/or gear components—not shown) within the handle housing 102 in order to perform various operations of the surgical device 100. The drive mechanism 106 (and/or components thereof) is operable to selectively articulate the end effector 300 about a longitudinal axis "X" defined by the adapter assembly 200 and relative to at least portions of the adapter assembly 200; to selectively rotate the end effector 300 about the longitudinal axis "X" and relative to the handle housing 102; to selectively move/approximate/separate an anvil assembly 310 and/or a cartridge assembly 320 of the end effector 300 with respect to one another; and/or to fire a stapling and cutting cartridge or reload 330 within the cartridge assembly 320 of end effector 300.

The handle housing 102 of the surgical device 100 includes an upper housing portion 102a that houses various components of the surgical device 100, and a lower hand grip portion 102b that extends from the upper housing portion 102a. The lower hand grip portion 102b of the handle housing 102 may be disposed distally of a proximal-most end of the upper housing portion 102a of the handle housing 102. The location of the lower hand grip portion 102b relative to the upper housing portion 102a is selected to balance a weight of the surgical device 100 while the surgical device 100 is connected to, or supports, the adapter assembly 200 and/or the end effector 300.

A connection portion 104 of the handle housing 102 is configured to secure to a proximal end portion of the adapter assembly 200. The connection portion 104 may include a contact surface 105 in electrical communication with the circuit board (not shown) of the surgical device 100 to control the drive mechanism 106. Each rotatable drive shaft 106a-106c of the drive mechanism 106 can be independently, and/or dependently, actuatable and rotatable. The rotatable drive shafts, 106a, 106b, and 106c may be arranged in a common plane or line with one another (e.g., a horizontal line). As can be appreciated, any number of rotatable drive shafts can be arranged in any suitable linear or non-linear configuration.

The handle housing 102 of the surgical device 100 supports finger-actuated control buttons, rocker devices, and/or the like for activating various functions of the surgical device 100. For example, the handle housing 102 may support actuators including an actuation pad 108 in operative registration with any number of sensors 108a that cooperate with the actuation pad 108 and/or actuators 107a, 107b to effectuate, for instance, opening, closing, rotating, articulating and/or firing of the end effector 300. The actuation pad 108 and/or the actuators 107a, 107b can be disposed in electrical communication with one or more motors 103a of the drive mechanism 106 to effectuate, for example, rotation of the rotatable drive shafts 106a, 106b, and/or 106c for actuation thereof to enable movement or manipulation of one or more of the components of the adapter assembly 200. Any of the presently described actuators can have any suitable configuration (e.g., button, knob, toggle, slide, etc.).

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009, the entire contents of each of which are incorporated herein by reference, for a detailed description of various internal components of and operation of exemplary electromechanical surgical systems, the components of which are combinable and/or interchangeable with one or more components of electromechanical surgical systems 10 described herein.

With reference to FIGS. 2-5, the adapter assembly 200 of the electromechanical surgical system 10 includes a housing 202 having a mounting assembly 202a at a proximal end portion thereof that couples to a distal end portion of the surgical device 100. The housing 202 further includes an outer housing 202b rotatably coupled to the mounting assembly 202a and surrounding an inner housing 202c. A shaft assembly 204 extends distally from the housing 202 along the longitudinal axis "X" of the adapter assembly 200 to a coupling member 206 of the adapter assembly 200 at a distal end portion of the adapter assembly 200. The coupling member 206 connects to a proximal end portion of the end effector 300.

The mounting assembly 202a of the housing 202 supports an electrical assembly 208 with electrical components (e.g., circuit board, pins, etc.) for electrical connection to a corresponding electrical plug (not shown) disposed in the connection portion 104 of the surgical device 100 (e.g., for calibration and communication of life-cycle information to the circuit board of the surgical device 100). The mounting assembly 202a includes a mounting button 212 that is spring biased toward an extended position and is configured to be depressed downwardly to a compressed position to selectively couple the mounting assembly 202a of the adapter assembly 200 to the connection portion 104 of the surgical device 100. The mounting button 212 includes sloped engagement features 212a that are configured to contact internal surfaces (not shown) of the connection portion 104 (FIG. 1) of the handle housing 102 while the mounting button 212 is in the extended position to facilitate securement of the housing 202 of the adapter assembly 200 to the connection portion 104 of the handle housing 102. Depression of the mounting button 212 moves the sloped engagement features 212a (FIG. 4) away from the connection portion 104 of the surgical device 100 so that the adapter assembly 200 can be selectively coupled and uncoupled to the surgical device 100. For a detailed description of similar electrical and mounting assemblies, reference can be made to U.S. Patent Application Publication No. 2015/0157320, filed Nov. 21, 2014, the entire contents of which are incorporated by reference herein.

Figure 5:
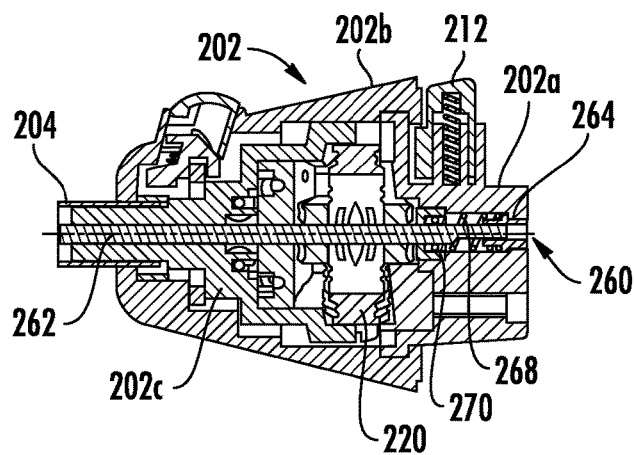
FIG. 5 is a cross-sectional view of the proximal portion of the adapter assembly shown in FIG. 3, as taken along section line 5-5 of FIG. 4.
Figure 6:
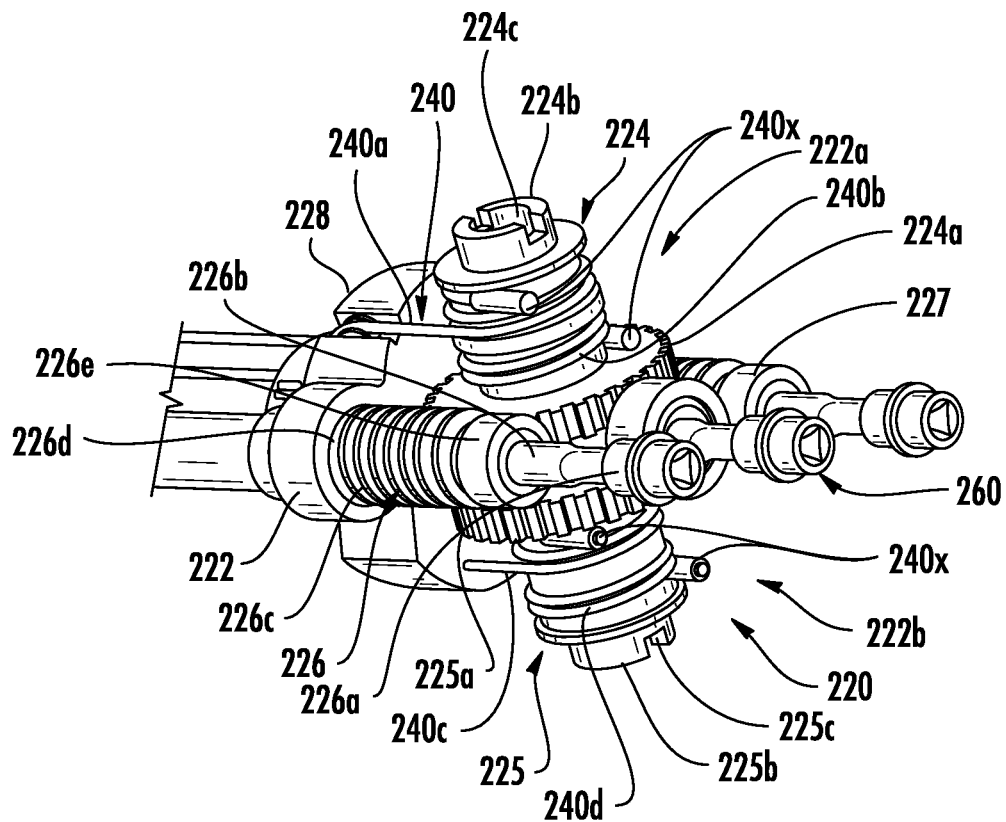
FIGS. 6 and 7 are perspective views of internal components of the proximal portion of the adapter assembly shown in FIG. 3 with some components thereof removed or shown in phantom for clarity.
Figure 7:
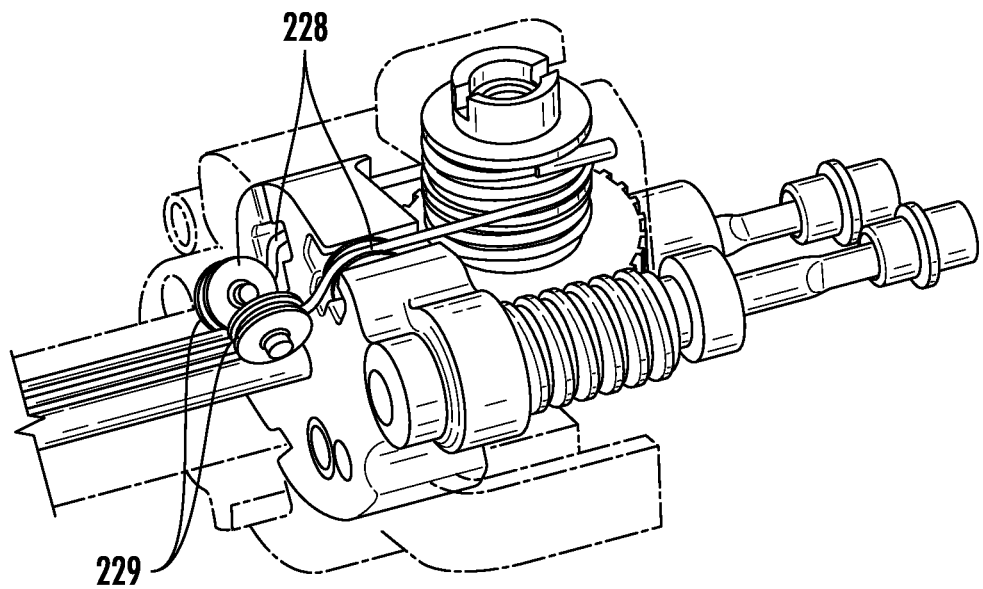

With reference to FIGS. 5-7, the housing 202 also supports an articulation or cable drive assembly 220 that includes cables 240 configured to manipulate the end effector 300 (FIG. 1), for example, to articulate the end effector 300 relative to the adapter assembly 200. The cable drive assembly 220 further includes a body portion 222, a first cable gear assembly 224, a second cable gear assembly 225, a first worm gear drive assembly 226, and a second worm gear drive assembly 227 that are rotatably supported on the body portion 222 of the cable drive assembly 220 to manipulate the cables 240.

Figure 23:
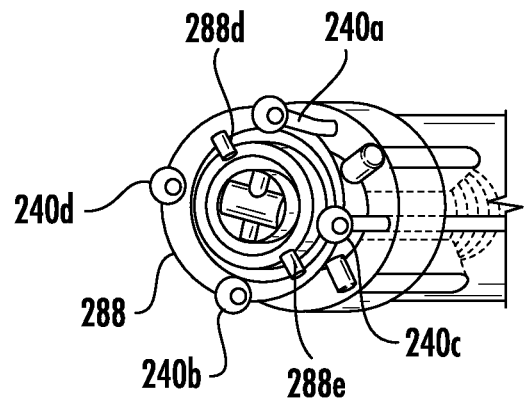
Figure 24:
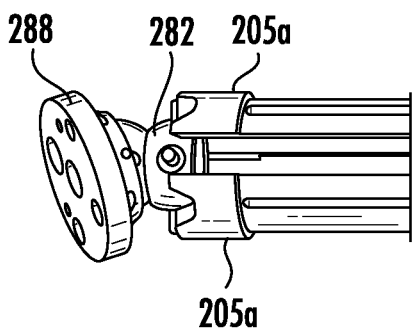
Figure 25:
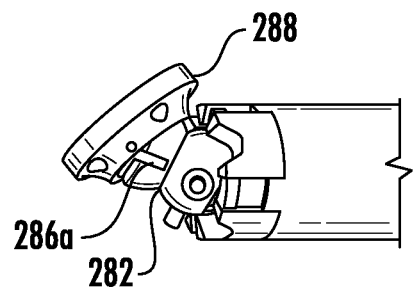

The first cable gear assembly 224 of the cable drive assembly 220 includes an upper gear 224a, an upper capstan 224b supported on the upper gear 224a, and an upper fastener 224c that couples the upper capstan 224b to the upper gear 224a while the upper capstan 224b is coupled to an upper portion 222a of the body portion 222 of the cable drive assembly 220. Similarly, the second cable gear assembly 225, which mirrors first cable gear assembly 224, includes a lower gear 225a, a lower capstan 225b supported on lower gear 225a, and a lower fastener 225c that couples the lower capstan 225b to the lower gear 225a while the lower capstan 225b is coupled to a lower portion 222b of the body portion 222 of cable drive assembly 220. The cables 240, which may include first, second, third, and fourth cables 240a, 240b, 240c, 240d (FIG. 23), are wound around respective upper and lower capstans 224b, 225b and have proximal end portions that are fixed to the respective capstans 224b, 225b via ferrules 240x. The cables 240a, 240b positioned on the first gear assembly 224 may be positioned to effectuate pitch (e.g., north-south direction) while the cables 240c, 240d positioned on the second gear assembly 225 may be positioned to effectuate yaw (e.g., east-west direction). Alternatively, the cables 240a, 240b may be positioned to effectuate yaw while cables 240c, 240d may be positioned to effectuate pitch.

The cable drive assembly 220 further includes proximal guide pulleys 228 that are rotatably supported within the body portion 222 of the cable drive assembly 220 and distal guide pulleys 229 that are rotatably supported by the inner housing 202c adjacent to the body portion 222 of the cable drive assembly 220. The proximal and distal guide pulleys 227, 229 function to reduce friction along the cables 240 and to guide the cables 240 along the adapter assembly 200 as the cables 240 translate along the proximal and distal guide pulleys 227, 229 while the respective proximal and distal guide pulleys 227, 229 rotate. The cables 240 extend from the first and/or second cable gear assemblies 224, 225 and are partially wound around the respective proximal and distal guide pulleys 228, 229 to reduce friction as the cables 240 translate along the guide pulleys 228, 229. One or more of the cables 240 may be wrapped in opposite directions around the proximal and/or distal guide pulleys 228, 229. The cables 240 extend from the guide pulleys 228, 229 and along a length of the shaft assembly 204. The cables 240 extend distally to ferrules 240y (FIG. 9) that operatively couple to a proximal end portion of the coupling member 206 to enable the coupling member 206 to selectively articulate relative to the shaft assembly 204 as the cables 240 are tightened/drawn/retracted (e.g., length of cable shortened) and/or released/let out (e.g., length of cable elongated).

The first worm gear drive assembly 226 of the cable drive assembly 220 is rotatably coupled to the first cable gear assembly 224 of the cable drive assembly 220 to rotate the first cable gear assembly 224 relative to the body portion 222 of the cable drive assembly 220. The first worm gear drive assembly 226 includes a drive coupler 226a supported on proximal portion of a shaft member 226b and rotatable to cause the shaft member 226b to rotate. The drive coupler 226a may have a tri-lobed configuration and is spring biased (spring not shown) within the mounting assembly 202a to enable the drive coupler 226a to slidably move along a proximal portion of the shaft member 226b between compresed and uncompressed positions to facilitate selective interconnection with one of the rotatable drive shafts 106 (e.g., rotatable drive shaft 106c) of the surgical instrument 100. The shaft member 226b extends distally to a worm gear 226c that rotates in response to rotation of the shaft member 226b and is supported by between bearings 226d, 226e. The second worm gear drive assembly 227 includes identical components to the first worm gear drive assembly 226 except that the second worm gear drive assembly 227 of cable drive assembly 220 is rotatably coupled to the second gear assembly 225 of the cable drive assembly 220 to rotate the second cable gear assembly 225 relative to the body portion 222. For a more detailed description of an exemplary cable drive assembly (or components thereof), reference can be made to U.S. Provisional Patent Application No. 62/333, 584, filed May 9, 2016, the entire content of which is incorporated by reference herein.

With reference to FIGS. 8-10B, the shaft assembly 204 of the adapter assembly 200 includes an outer tube 204a and an inner shaft assembly 204b supported by the outer tube 204a. The inner shaft assembly 204b includes a proximal inner shaft 204c that extends distally from the housing 202 to a support ring 204d. The proximal inner shaft 204c is hollow. The support ring 204d of the inner shaft assembly 204b defines apertures 204e therethrough that are configured to receive the cables 240 to maintain the cables 240 at predetermined locations along the shaft assembly 204 (e.g., four cables positioned at circumferentially spaced locations such as Northerly, Southerly, Easterly, and Westerly locations, respectively). The cables 240 may twist along the length of the adapter assembly 200. The inner shaft assembly 204b further includes a distal guide shaft 205 that extends distally from the support ring 204d.

With reference to FIGS. 9, 10A, 10B, 19, and 20, the distal guide shaft 205 of the shaft assembly 204 includes arms 205a that are circumferentially spaced relative to one another about the longitudinal axis "X." Each of the arms 205a extends to a distal crown 205b and defines a cable lumen 205c therethrough that is configured to receive one of the cables 240 therein. The distal crown 205b includes a first prong 205d and a second prong 205e that together define a central arched recess 205f between one another. The distal guide shaft 205 further defines a central bore 205g and finger recesses 205h that are circumferentially spaced about distal guide shaft 205 between adjacent distal crowns 205b. The central bore 205g and the finger recesses 205h are configured to slidably receive a finger spring assembly 207.

Figure 19:
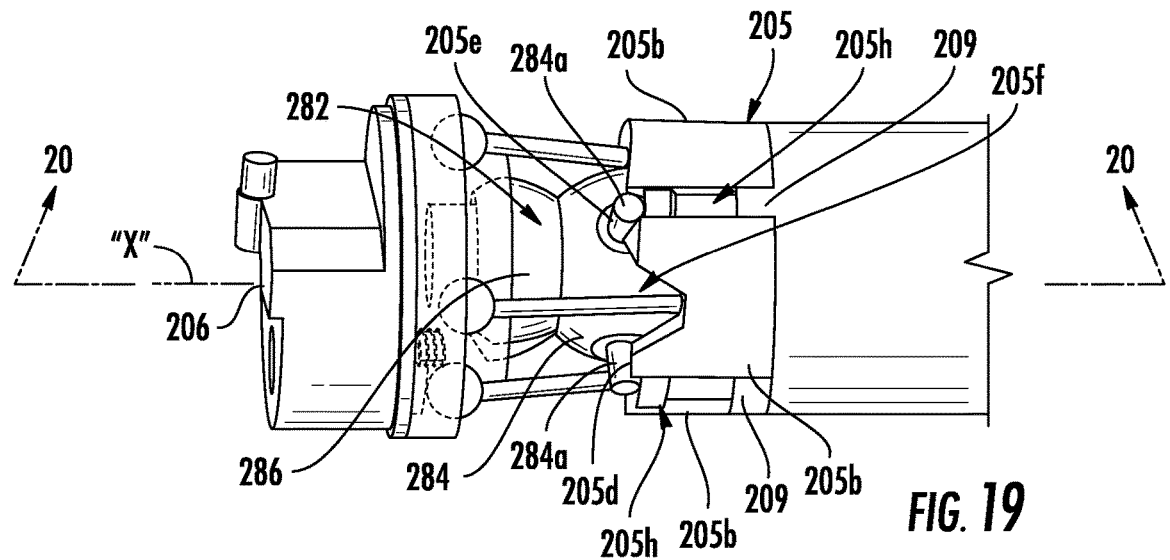
FIG. 19 is an enlarged, perspective view of a distal portion of the adapter assembly of FIG. 3, the distal portion shown in an unarticulated position.
Figure 20:
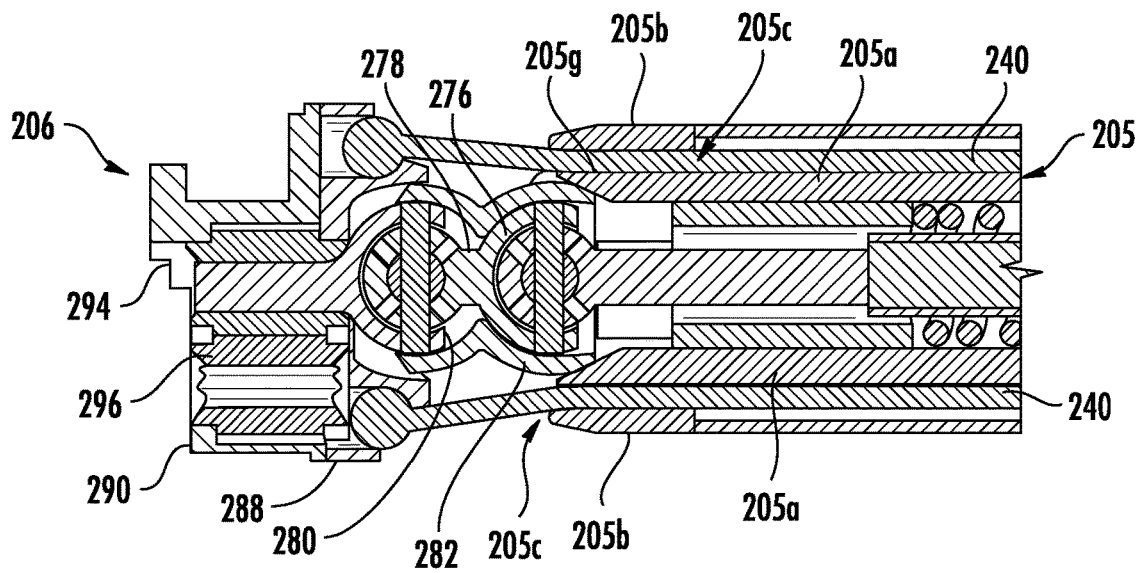
FIG. 20 is a cross-sectional view of the distal portion of the adapter assembly shown in FIG. 19, as taken along section line 20-20 of FIG. 19.
Figure 21:
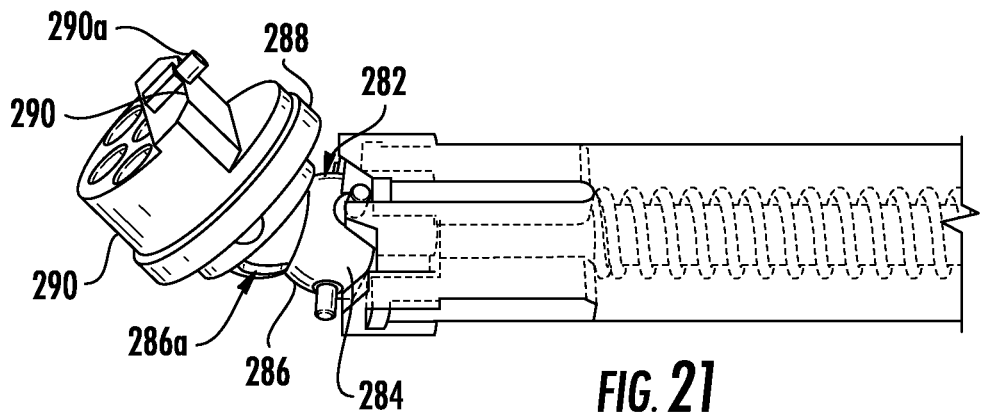
FIGS. 21-27 are various views of distal portions of the adapter assembly showing the adapter assembly and/or components thereof in articulated and unarticulated positions.
Figure 22:
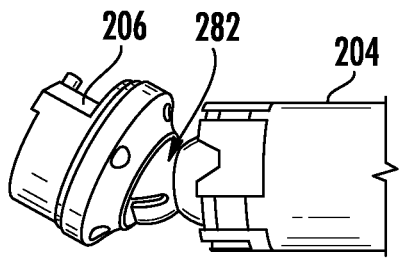

The finger spring assembly 207 is slidably movable between uncompressed and compressed positions to accommodate articulating movement of a joint housing 282 (see FIGS. 21-25). The finger spring assembly 207 includes a finger member 207a having fingers 207b slidably supported in the finger recesses 205h of the distal guide shaft 205, and a finger spring 207c supported in the central bore 205g against a support wall 205i of the distal guide shaft 205. The finger spring 207c is coupled to the finger member 207a to spring bias the finger member 207a distally so that the finger spring 207c urges the finger assembly 207 toward the uncompressed position. Proximal portions of the finger recesses 205h are configured to receive teeth 209 (FIG. 19)

that extend distally from the outer tube 204a to secure the outer tube 204a to the distal guide shaft 205.

With reference to FIGS. 11-15, the adapter assembly 200 further includes a manual rotation mechanism 250 operatively coupled to the housing 202 of the adapter assembly 200. The rotation mechanism 250 includes a depressible actuator 252 (e.g., a button or the like) mounted to the outer housing 202b, a locking blade 254 that is movably coupled to the actuator 252 between extended and retracted positions via springs 256, and a locking ring 258 fixed around an outer surface of the inner housing 202c and selectively engagable with the locking blade 254 as the locking blade 254 moves between the extended and retracted positions. The actuator 252 defines an angled lateral recess 252a, which may extend through opposite sides of the actuator 252, and an elongate slot 252b. The actuator 252 may further include indicia 252c (e.g., arrows to indicate rotation direction). The actuator 252 further includes a foot 252d that is configured to engage the locking blade 254 to limit approximating movement of the actuator 252 toward the locking blade 254.

The locking blade 254 of the rotation mechanism 250 includes one or more posts 254a that extend laterally therefrom and are slidable along the angled lateral recess 252a of the actuator 252 as the actuator 252 and the locking blade 254 move relative to one another in response to compression and/or release of the actuator 252. The locking blade 254 further includes a horn 254b that is slidably received in the elongate slot 252b of the actuator 252 (e.g., vertically slidable) to maintain the locking blade 254 in alignment with the actuator 252 as the actuator 252 and the locking blade 254 move relative to one another in response to compression and/or release of the actuator 252. The locking blade 254 further includes a stop flange 254c that limits proximal movement of the locking blade 254 and a locking heel 254d that selectively engages the locking ring 258 to prevent the housing 202 from rotating relative to the locking ring 258. The locking blade 254 defines a rotation recess 254d therein that is positionable in registration with the locking ring 258 as the locking blade 254 axially translates relative to the locking ring 258 upon compression and/or release of the actuator 252. With the rotation recess 254d disposed in registration with the locking ring 258, the rotation recess 254d is configured to enable the locking blade 254 to rotate about the locking ring 258 as the outer housing 202b of the housing 202 rotates about the inner housing 202c of the housing 202. The locking blade 254 further includes a support shoulder 254f that is selectively engageable with the foot 252d of the actuator 252 to limit approximating movement of the actuator 252 toward the locking ring 258 when the actuator 252 is depressed (e.g., actuation/compression of the actuator 252).

Figure 11:
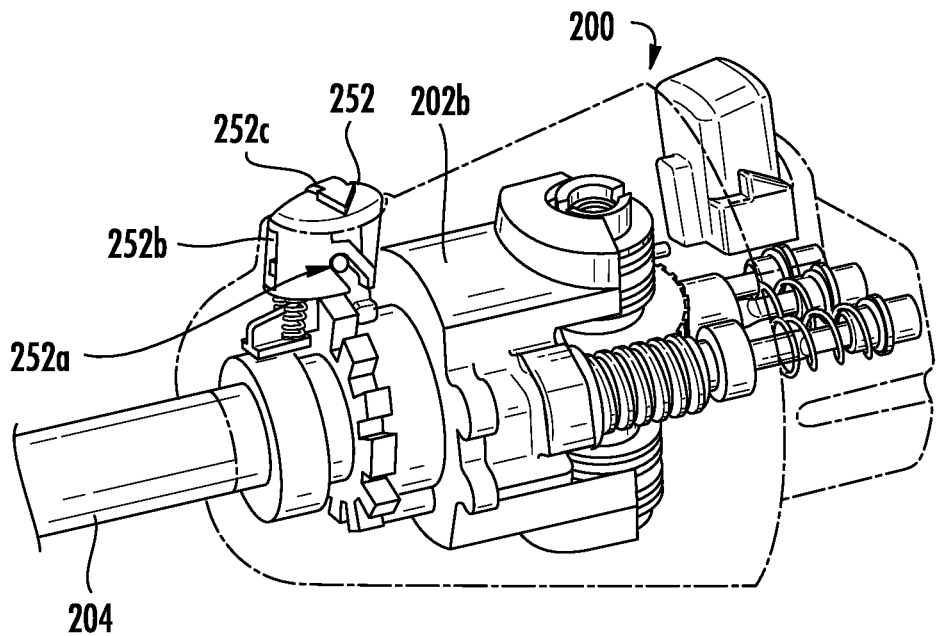
FIGS. 11-15 are progressive views of portions of the adapter assembly of FIG. 3 illustrating operation of a rotation mechanism of the adapter assembly.
Figure 12:
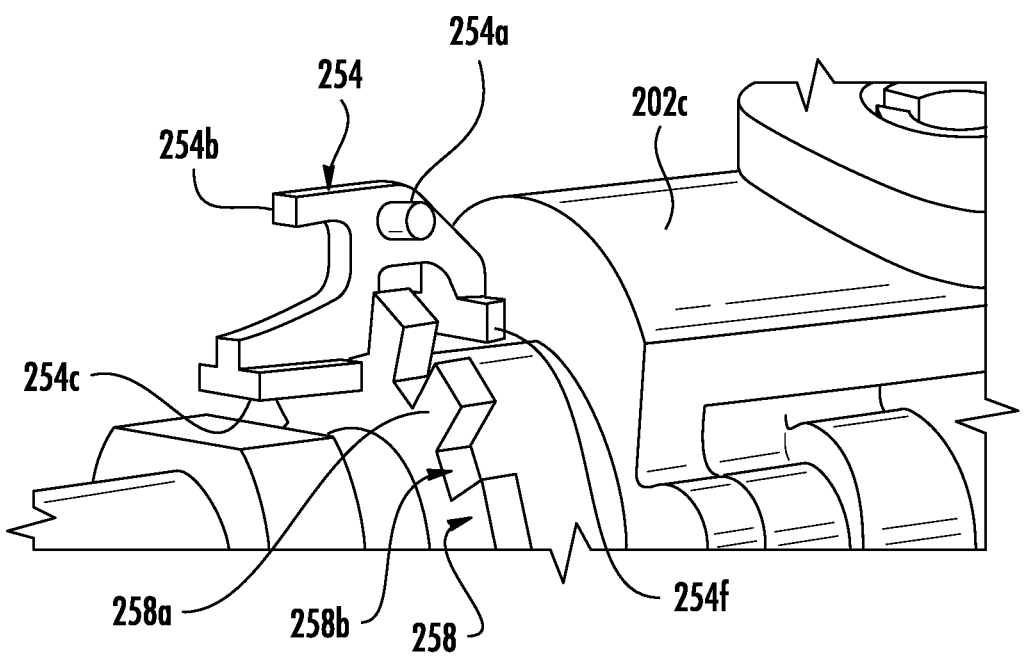
Figure 13:
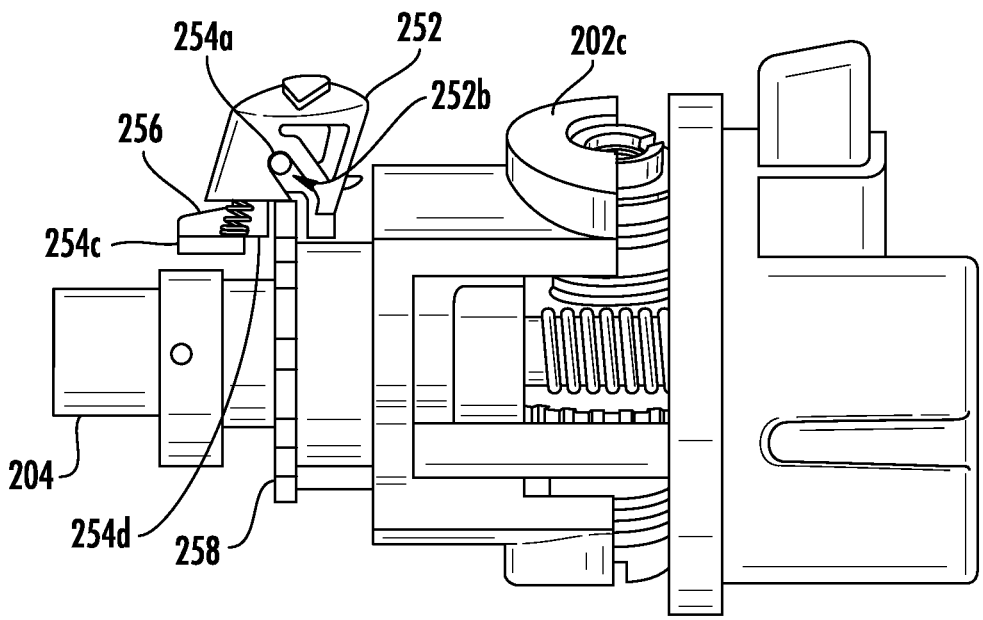
Figure 14:
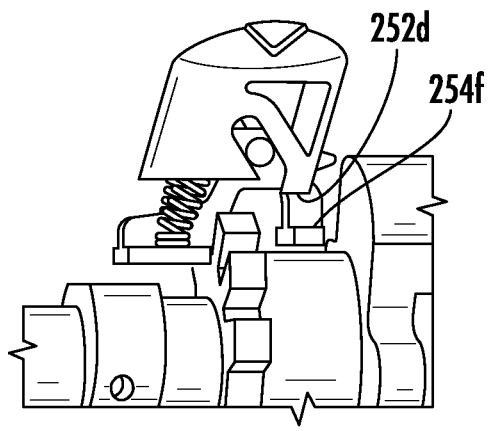
Figure 15:
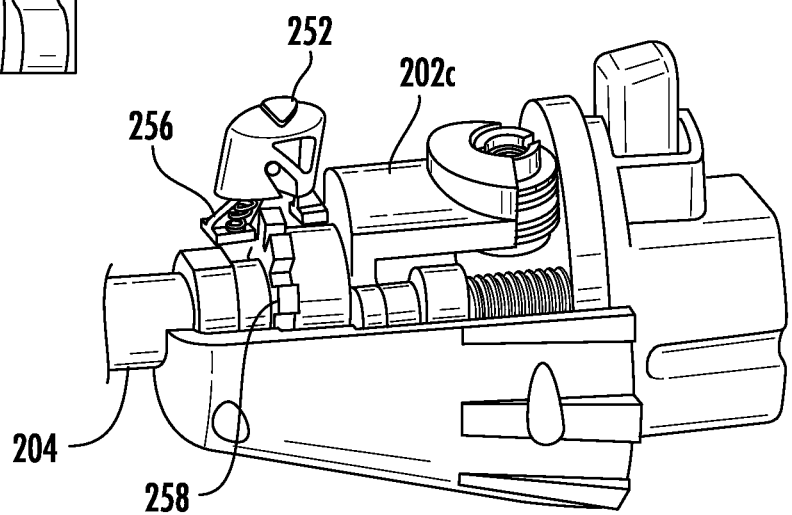

The locking ring 258 of the rotation mechanism 250 includes spaced-apart teeth 258a that define openings 258b between adjacent teeth 258a. Each of the openings 258b of the locking ring 258 is configured to receive the heel 254d of the locking blade 245 when the actuator 252 is unactuated (FIGS. 11 and 15). While the actuator 252 is unactuated, side surfaces of two adjacent teeth 258a of the locking ring 258 are configured to laterally contact opposing side surfaces of the heel 254d of the locking blade 254 to prevent the outer housing 202b of the housing 202 from rotating (in either direction—clockwise or counterclockwise) about the inner housing 202c of the housing 202 to thereby prevent concomitant rotation of the shaft assembly 204 about the longitudinal axis "X" of the adapter assembly 200.

In use, to effectuate a rotation of the end effector 300 about the longitudinal axis "X" (FIG. 1) of the adapter assembly 200, the actuator 252 of the rotation mechanism 250 is actuated or depressed radially inward toward the locking ring 258, compressing the springs 256 of the rotation mechanism 250 so that the locking blade 254 moves distally along the longitudinal axis "X." As the locking blade 254 moves distally, the posts 254a of the locking blade 254 slide along the angled lateral recess 252a of the actuator 252 so that the heel 254d of the locking blade 245 separates from the locking ring 258, whereby the rotation recess 254d longitudinally aligns with the locking ring 258. Once the rotation recess 254d of the locking blade 254 is longitudinally aligned with the locking ring 258, the outer housing 202b of the housing 202 is rotationally unlocked so that it can be rotated about the longitudinal axis "X," to thereby rotate the shaft assembly 204 and the end effector 300 about the longitudinal axis "X."

Once a desired rotational orientation of the outer housing 202b about the circumference of the locking ring 258 is established, the actuator 252 can be released so that the springs 256 urge the actuator 252 and the locking blade 254 into their unactuated positions to rotationally lock the heel 254d of the locking blade 254 between two adjacent teeth 258a of the locking ring 258 and fix the rotational orientation of the shaft assembly 204 and end effector 300. Each pair of adjacent teeth 258a of the locking ring 258 defines an opening 258b that is configured to receive the heel 254d of the locking blade 254 such that each opening 258b is disposed at a different rotational orientation than the other openings 258b so that the housing 202, the shaft assembly 204, and the end effector 300 can be simultaneously rotationally locked at different rotational orientations about the longitudinal axis "X" (e.g., any circumferential location).

With reference to FIGS. 5, 10B, and 16-18, the adapter assembly 200 further includes a firing assembly 260 having a proximal portion supported in the housing 202 and a distal portion that extends to the coupling member 206. The firing assembly 260 includes a drive shaft 262 that supports an input coupler 264 on a proximal portion of the drive shaft 262, and a joint assembly 266 on a distal portion of the drive shaft 262. The input coupler 264 may have a tri-lobe configuration and is supported within the mounting assembly 202a. The input coupler 264 is slidably movable along the proximal portion of the drive shaft 262 and biased by a spring 268 between uncompressed and compressed positions to facilitate selective interconnection with the rotatable drive shaft 106b of the surgical device 100. The drive shaft 262 is rotatably mounted within the housing 202 by a bearing 270 and extends centrally through the housing 202 to the joint assembly 266.

As seen in FIG. 16-18, a proximal portion of the joint assembly 266 is pinned to a distal portion of the drive shaft 262 via a pin 272. The joint assembly 266 includes a first or proximal shaft 274 that extends distally from the drive shaft 262 to a first joint 276. The first joint 276 includes a ball 276a and a socket 276b that are coupled together via pins 276c, 276d. Although the socket 276b of the first joint 276 may have any suitable configuration, the socket 276b may include a hemispherical configuration to facilitate movement of the socket 276b about the ball 276a. In embodiments, the first joint enables movement through 180°; in other embodiments, through 90°; in yet other embodiments, through 70°. The pins 276c, 276d may be transversely oriented with respect to one another (e.g., orthogonal). The ball 276a of the first joint 276 defines an elongated slot 276e in registration with the pin 276d. The ball 276a further defines a transverse channel 276f that is transverse to the elongated slot 276e and rotatably receives the pin 276c therein. Although any configuration is contemplated, the transverse channel 276f of the ball 276a may have a circular cross-section and/or a cylindrical shape. The pin 276d of the first joint 276 is pivotable within the elongated slot 276e about a long axis "A" defined by the pin 276c (and along longitudinal axis "X") as the pin 276c rotates about the long axis "A" to move the socket 276b of the first joint 276 about the ball 276a of the first joint 276, as indicated by arrow "aa." The pin 276c may be configured to remain coaxial with the long axis "A" as the pin 276c rotates about the long axis "A."

The joint assembly 266 further includes a second or connector shaft 278 that extends distally from a distal portion of the socket 276b of the first joint 276. The second shaft 278 extends distally to a second joint 280 of the joint assembly 266.

The second joint 280 of the joint assembly 266 includes a ball 280a and a socket 280b that are coupled together by pins 280c, 280d. Although the socket 280b may have any suitable configuration, the socket 276b may include a hemispherical configuration to facilitate movement of the socket 280b about the ball 280a. In embodiments, the second joint enables movement through 180°; in other embodiments, through 90°; in yet other embodiments, through 70°. The pins 280c, 280d may be transversely oriented with respect to one another (e.g., orthogonal). The ball 280a of the second joint 280 defines an elongated slot 280e in registration with the pin 280d. The ball 280a also defines a transverse channel 280f that is transverse to the elongated slot 280e and rotatably receives the pin 280c therein. Although any configuration is contemplated, the transverse channel 280f may have a circular cross-section and/or a cylindrical shape. The pin 280d is linearly pivotable within the elongated slot 280e about a long axis "B" defined by the pin 280c as the pin 280c rotates about the long axis "B" to move the socket 280b of the second joint 280 about the ball 280a of the second joint 280, as indicated by arrow "bb." The pin 280c may be configured to remain coaxial with the long axis "B" as the pin 280c rotates about the long axis "B." The second joint 280 further includes a drive pin 280g that extends distally from the socket 280b and rotatably couples to the coupling member 206. The drive pin 280g has a noncircular transverse cross-section and includes a flat surface 280h.

The first and second joints 276, 280 are configured to act as one or more universal joints to enable articulation of the end effector 300 relative to the shaft assembly 204. In embodiments, the first and second joints collectively enable movement through 180°; in other embodiments, through 90°; in yet other embodiments, through 70° in any one direction.

With reference to FIGS. 19-29, the joint assembly 266 further includes a joint housing 282 supported on the first and second joints 276, 280 to enable the first and second joints 276, 280 to move multi-axially therein (e.g., pivot and/or rotate). The joint housing 282 may include an hourglass configuration to facilitate the multi-axial movement of one or both joints 276, 280. The joint housing 282 includes a proximal housing 284 that pivotably and rotatably supports the first joint 276 therein, and a distal housing 286 that pivotably and rotatably supports the second joint 280 (and the connector shaft 278) therein. The proximal housing 284 includes nubs 284a that extend radially outward from an outer surface of the proximal housing 284 and are positioned in registration with distal portions of the finger recesses 205h of the distal guide shaft 205, whereby the distal portions of the finger recesses 205h are configured to selectively receive the nubs 284a therein (e.g., linearly and non-rotatably) as the joint housing 282 articulates relative to the distal guide shaft 205. In embodiments, joint housing, 282, in conjunction with first and second joints 276, 280, permits articulating movement through 270°; in other embodiments, through 180°; in yet other embodiments, through 90°.

The nubs 284a of the proximal housing 284 are configured to selectively contact respective fingers 207b of the finger spring assembly 207 to compress the finger member 207a against the finger spring 207c in response to articulation of the coupling member 206/joint assembly 266 to enable the second joint 280 of the joint assembly 266 to pivot to a maximum articulation before the first joint 276 of the joint assembly 266 begins to move toward its maximum articulation (e.g., sequentially) by virtue of a spring load imposed by the finger spring assembly 207 on the nubs 284a of the joint housing 282 of the joint assembly 266. The contact between the fingers 207b of the finger spring assembly 207 and the nubs 284a of the joint housing 282 ensures that the first and second joints 276, 280 consistently articulate in the same order (e.g., whereby the nubs 284a/finger spring assembly 207 function to sequence articulating movement of the joints 276, 280). Furthermore, the nubs 284a also function to prevent rotation between the shaft assembly 204 and the joint housing 282 as the nubs 284a are received between distal portions of the finger recesses 205h of the distal guide shaft 205 of the shaft assembly 204. The proximal housing 284 of the joint housing 282 may define any number of nubs 284a such as four nubs 284a circumferentially spaced about the proximal housing 284 to correspond with four finger recesses 205h. The distal housing 286 of the joint housing 282 extends distally from the proximal housing 284 of the joint housing 282 and is disposed in mirrored relation with the proximal housing 284. The distal housing 286 defines housing slots 286a configured to facilitate articulation of the coupling joint 206 about the distal housing 286.

The coupling member 206 of the adapter assembly 200 includes a socket plate 288 and an attachment plate 290 that are coupled together via fasteners 292a, 292b. The coupling member 206 supports an input coupler 294, which may be centrally disposed within the coupling member 206, and an output coupler 296 disposed in vertical registration with, and enmeshed with, the input coupler 294.

Figure 26:
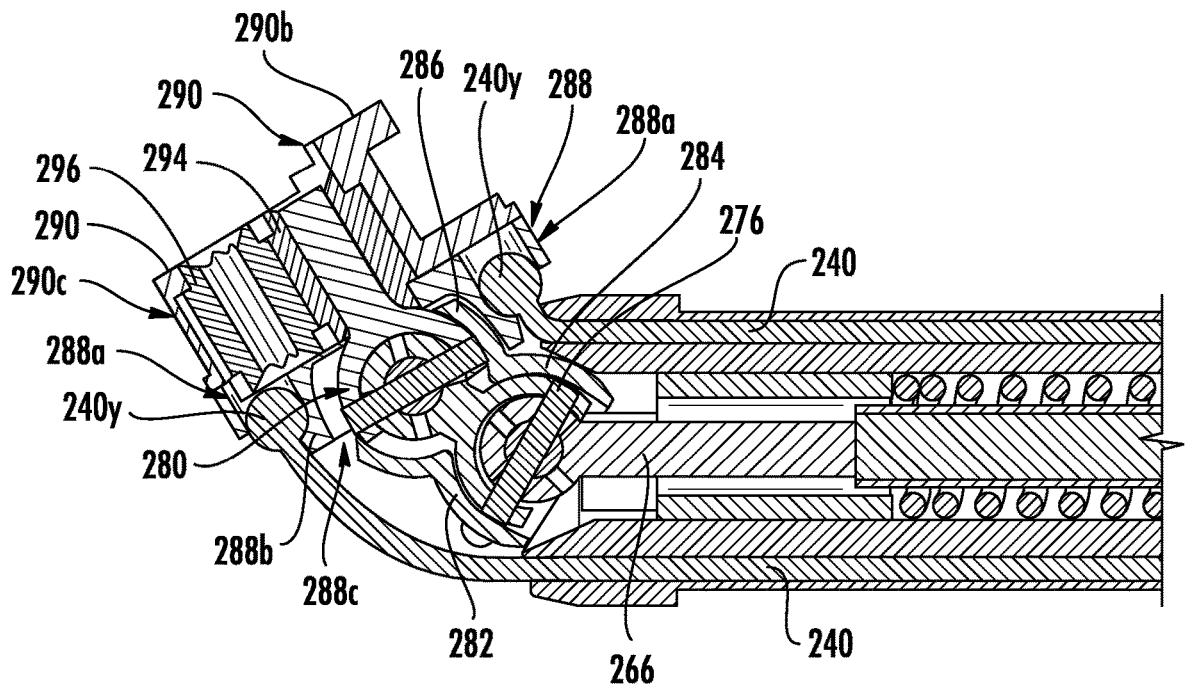
Figure 27:
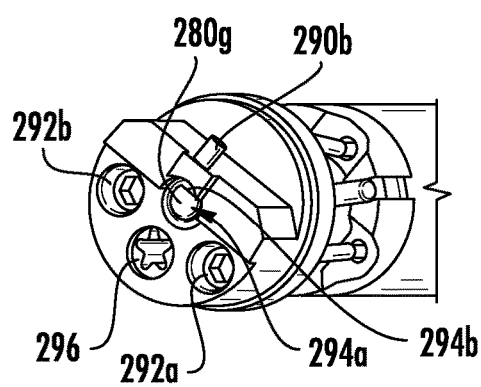
Figure 28:
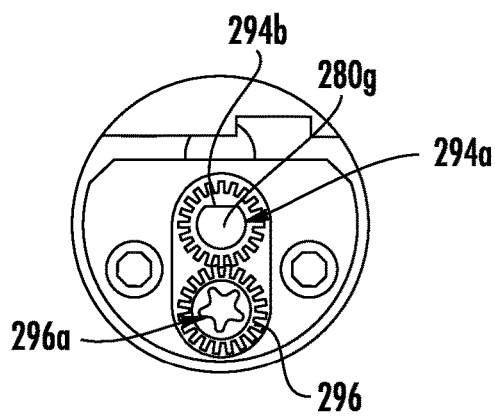
FIG. 28 is an enlarged, cross-sectional view of the end effector of the electromechanical surgical system of FIG. 1, as taken along section line 28-28 of FIG. 1.
Figure 29:
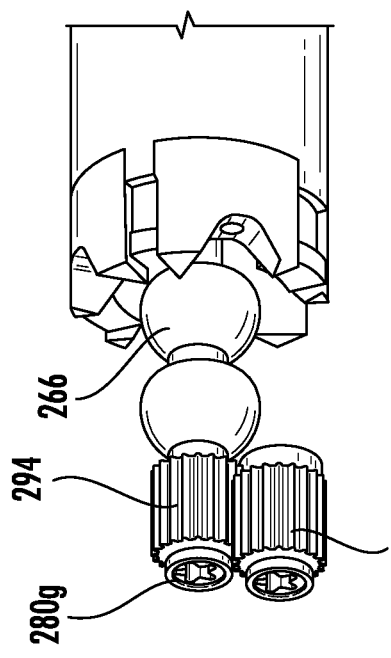
FIG. 29 is an enlarged, perspective view of a distal portion of the adapter assembly of FIG. 3 with portions shown in phantom for clarity.
Figure 30:
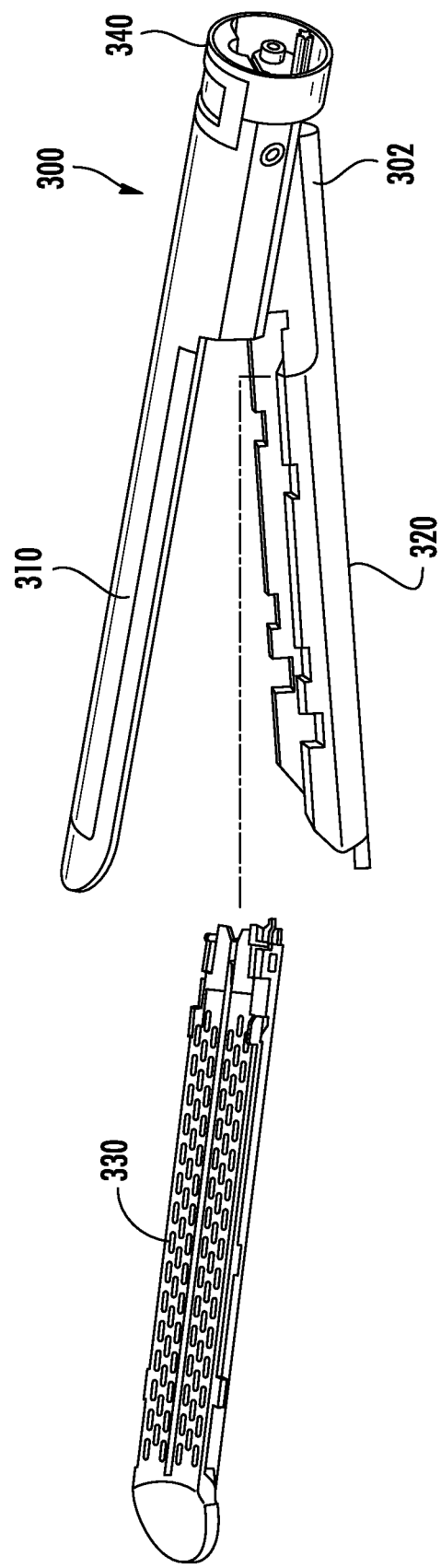

With specific reference to FIG. 26, the socket plate 288 defines ferrule recesses 288a (e.g., four) that are circumferentially spaced about a proximal portion of the socket plate 288 and are configured to receive the ferrules 240y secured to distal ends of the respective cables 240 to secure the ferrules 240y within the ferrule recesses 288a. The ferrules 240y, which may have a rounded or spherical configuration, are multi-axially movable (e.g., rotatable and/or pivotable) within the ferrule recesses 288a to facilitate articulating movement of the coupling member 206 relative to the shaft assembly 204. The socket plate 288 includes an annular lip 288b that extends proximally from the plate 288 and circumscribes a socket 288c that multi-axially (e.g., rotatably and/or pivotably) receives the second joint 280 of the joint assembly 266 therein and pivotably and non-rotatably receives the distal housing 286 of the joint housing 282 therein. The socket plate 288 further includes pins 288d, 288e that extend radially inward from the annular lip 288b and are configured to slide linearly through the housing slots 286a of the distal housing 289 of the joint housing 282 to facilitate articulating movement of the coupling member 206 about the joint housing 282 while preventing rotation between the coupling member 206 and the joint housing 282.

With continued reference to FIG. 26, the attachment plate 290 of the coupling member 206 includes a platform 290a having a post 290b extending transversely therefrom (e.g., orthogonally). The attachment plate 290 also defines a coupler chamber 290c that rotatably supports the input and output couplers 294, 296, as well as the drive pin 280g of the second joint 280 therein. The input and output couplers 294, 296 are disposed within the coupler chamber 290c in vertical registration with one another with the drive pin 280g mounted within the input coupler 294. The input coupler 294 includes an inner surface 294b which may be at least partially flat and which may correspond to an outer surface of the drive pin 280g. The inner surface 294b defines a non-circular opening 294a that is configured to receive the drive pin 280g of the second joint 280 so that the drive pin 280g and the input coupler 294 are positioned to rotate together in the same direction in response to rotation of the drive pin 280g. The input and output couplers 294, 296 are positioned in the coupler chamber 290c to rotate in opposite directions as the drive pin 280g rotates the input coupler 294 therein. The output coupler 296 also includes an inner surface that defines a non-circular opening 296a. The non-circular opening 296a may have a torque head configuration (e.g., star) or the like configured to receive a proximal portion of the end effector 300 to fire the end effector 300 upon rotation of the output coupler 296. The input and output couplers 294, 296 may be in the form of gears having any number and/or configuration of teeth extending radially therefrom about a respective circumference thereof, and which may enmesh with one or more teeth of the other of the input and output couplers 294, 296.

Turning now to FIGS. 30-33, the end effector 300, which may be in the form of single use loading unit or a multi-use loading unit, includes the anvil assembly 310 and the cartridge assembly 320, which are pinned together by pins 302. The cartridge assembly 320 is configured to selectively receive the stapling and cutting cartridge or reload 330 therein. The end effector 300 further includes a coupling assembly 340 mounted to a proximal end portion of the end effector 300 that selectively couples to the coupling member 206 of the adapter assembly 200.

Figure 33:
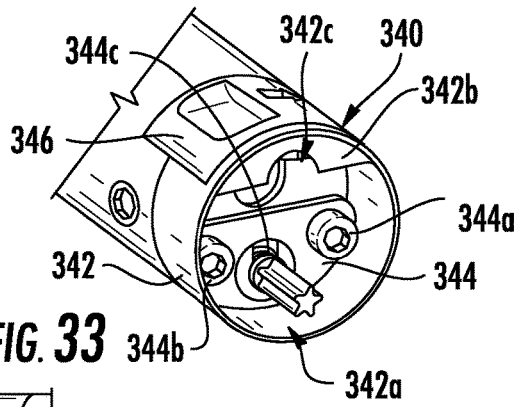
FIGS. 33-37 are progressive views illustrating the end effector of the electromechanical surgical system of FIG. 1 being coupled to the adapter assembly of FIG. 3.
Figure 34:
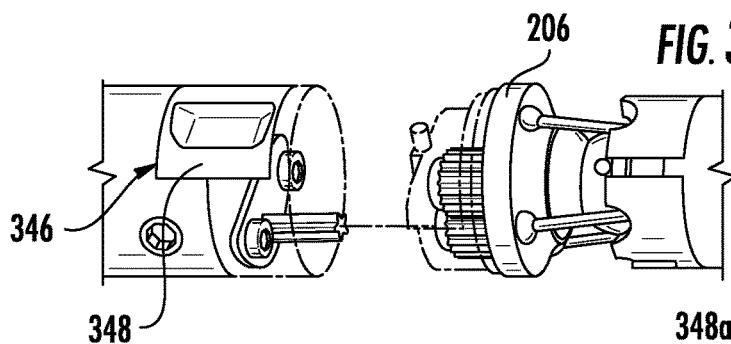
Figure 35:
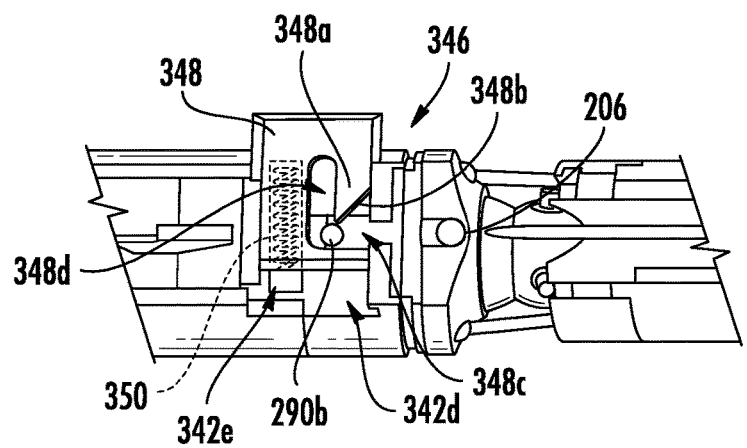
Figure 36:
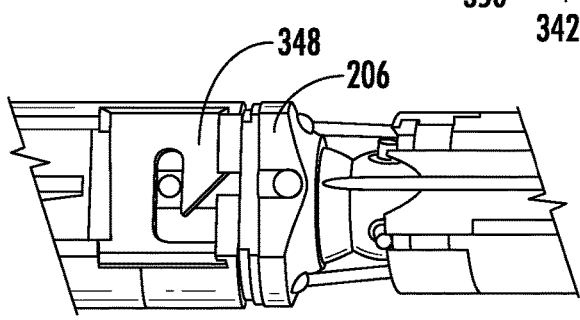
Figure 37:
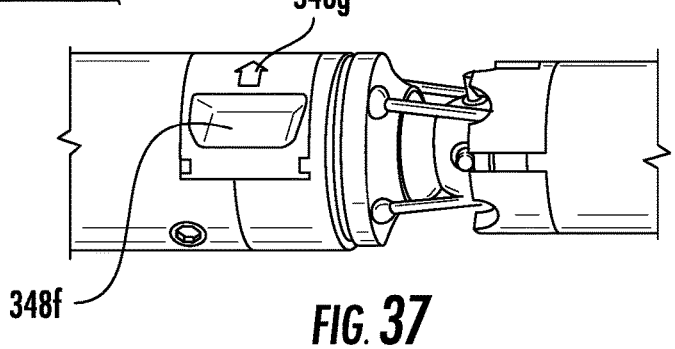

With reference to FIGS. 33-37, the coupling assembly 340 of the end effector 300 includes a coupling ring 342, a mounting plate 344, and a slide assembly 346. The coupling ring 342 defines a receiving chamber 342a that is configured to receive the attachment plate 290 of the coupling member 206 therein. The mounting plate 344 is supported in the receiving chamber 342a and is positioned to secure the coupling ring 342 to the proximal end portion of the cartridge and anvil assemblies 310, 320 of the end effector by fasteners 344a, 344b. The mounting plate 344 further defines a shaft opening 344c therethrough. The coupling ring 342 further includes an arch 342b that extends radially into the receiving chamber 342a and defines a post receiving recess 342c. The coupling ring 342 further defines a slide channel 342d and a spring pocket 342e in an outer surface of the coupling ring 342. The slide assembly 346 includes a slide member 348 that is slidably supported in the slide channel 342d of the coupling ring 342 between an open position (FIG. 35) to receive the post 290b of the coupling member 206, and a closed position to secure the post 290b against the slide member 348 of the slide assembly 346. The slide assembly 346 further includes a spring 350 that is supported within the spring pocket 342e of the coupling ring 342, and in abutment with the slide member 348, to spring bias the slide member 348 toward the closed position (FIGS. 33, 34, and 37). The slide member 348 is configured to compress the spring 350 as the slide member 348 is moved from the closed position toward the open position.

With reference to FIGS. 35-37, the slide member 348 of the slide assembly 346 includes an arm 348a having an angled face 348b. The slide member 348 further defines an insertion channel 348c in registration with the arm 348a and a locking channel 348d located adjacent to the arm 348a. The locking channel 348d is disposed transverse to the insertion channel 348c (e.g., orthogonally). The insertion channel 348c and the locking channel 348d are configured to slidably receive the post 290b of the coupling member 206 therein as the slide member 348 moves toward the open position. The locking channel 348d is configured to maintain the post 290b locked therein as the slide member 348 moves toward, and/or is disposed in, the closed position. The post 290b is configured to drive the slide member 348 from the closed position to the open position if the post 290b is driven into the angled face 348b of the slide member 348 upon insertion of the post 290b into the insertion channel 348c (e.g., snap-fit as opposed to manually sliding the slide member 348 open).

The slide member 348 further includes a finger recess 348f defined in an outer surface thereof that enables the slide member 348 to be manually slid from the closed position to the open position. While the orientation of the angled face 348b of the arm 348a enables the post 290b to drive the slide member 348 from the closed position to the open position upon insertion, once the post 290b is locked within the locking channel 348c, the slide member 348 must be manually moved to the open position until the post 290b is aligned with the insertion channel 348c so that the post 290b can be removed through the insertion channel 348c to separate the coupling assembly 340 of the end effector 300 from the coupling member 206 of the adapter 200. The slide member 348 may further include indicia 348g such as an arrow to indicate the direction for movement toward the open position.

Figure 38:
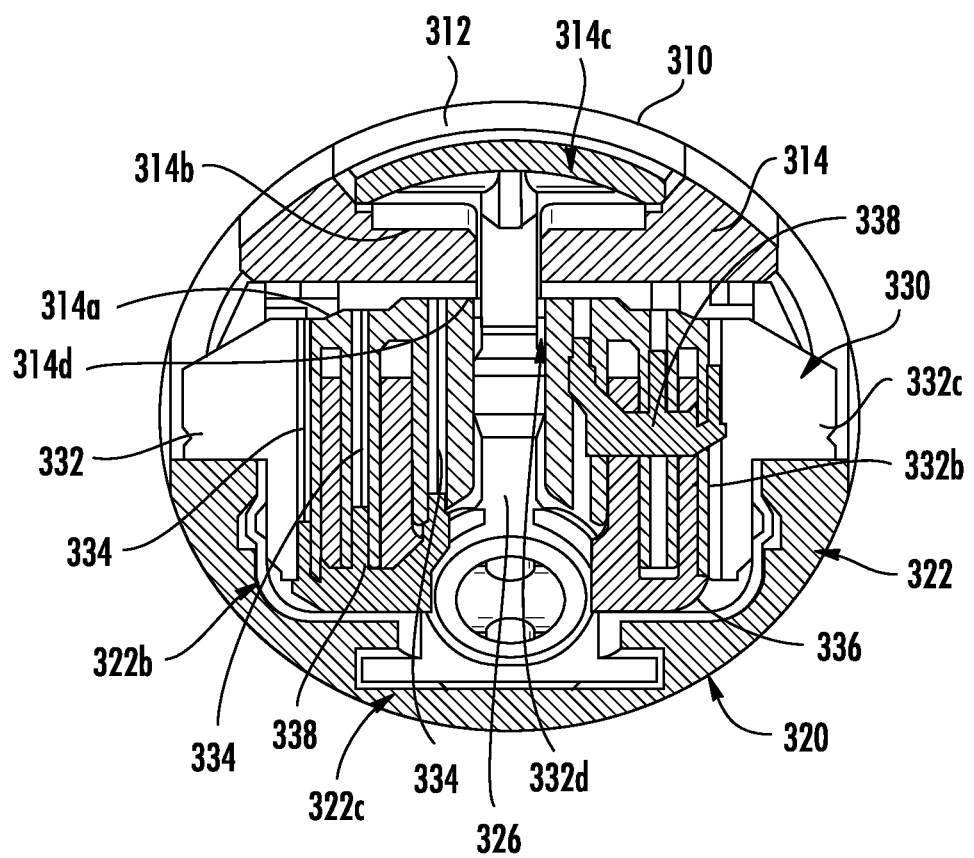
FIG. 38 is a cross-sectional view of the end effector of the electromechanical surgical system of FIG. 1, as taken along section line 38-38 of FIG. 1.
Figure 39:
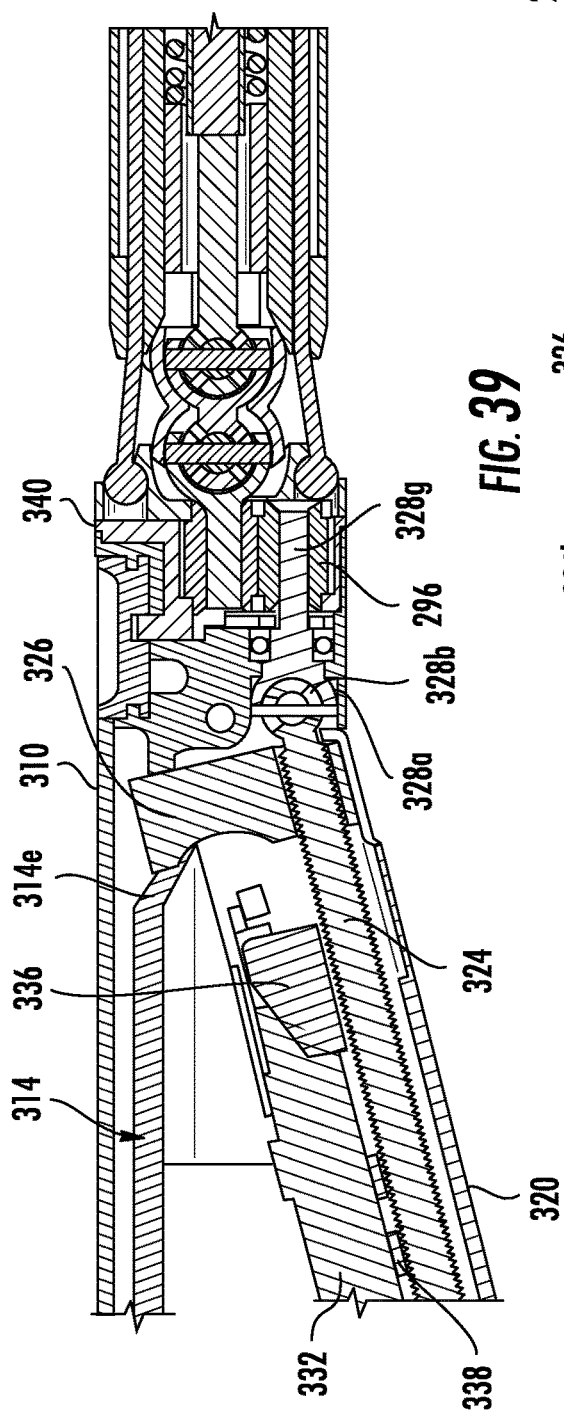
FIGS. 39-42 are progressive views illustrating a clamping and a firing of the end effector of the electromechanical surgical system of FIG. 1.

With reference to FIGS. 38 and 39, the anvil assembly 310 includes an anvil body 312 and an anvil plate 314 supported on the anvil body 312. The anvil plate 314 includes a tissue contact surface 314a defining fastener forming pockets (not shown) therein. The anvil plate 314 also includes a knife slide surface 314b that is disposed opposite to the tissue contact surface 314a. The knife slide surface 314b is spaced from the anvil body 312 by an upper knife passage 314c defined between the knife slide surface 314b and the anvil body 312. The anvil plate 314 defines a knife channel 314d that extends longitudinally through the anvil plate 314 between the knife slide surface 314b and the tissue contact surface 314a. The anvil plate 314 further includes a knife ramp 314e.

With reference to FIGS. 31, 32 and 38-40, the cartridge assembly 320 includes a support body 322 defining tab slots 322a configured to facilitate selective attachment of the reload 330 to the support body 322. The support body 322 further defines a support channel 322b configured to receive the reload 330 and a lower knife passage 322c that is disposed in vertical registration with the support channel 322b and the upper knife passage 314c of the anvil assembly 310. The cartridge assembly 320 supports a lead screw 324 that is threadably coupled to a drive beam 326. The lead screw 324 includes a drive joint 328 located at a proximal end portion of the lead screw 324. The drive joint 328 includes a ball member 328a secured to a proximal end of the lead screw 324 and a ball socket 328b that multi-axially receives the ball member 328a therein (e.g., rotatably and pivotably). The ball member 328a is pivotably and rotatably coupled to the ball socket 328b by pins 328c, 328d that are transversely arranged relative to one another. The ball member 328e further defines an elongate slot 328f within which the pin 328c pivots about an axis "C" defined through pin 328d, as indicated by arrow "cc." The ball socket 328b includes an input shaft 328g that extends proximally from the ball socket 328b and is received within the noncircular opening 296a of output coupler 296 of the coupling member 206.

The drive beam 326 of the cartridge assembly 320 includes a vertical member 326a having an upper flange 326b mounted to a first end of the vertical member 326a and foot 326c mounted to a second end of the vertical member 326a. The foot 326c includes a lower flange 326d extending therefrom.

Figure 41:
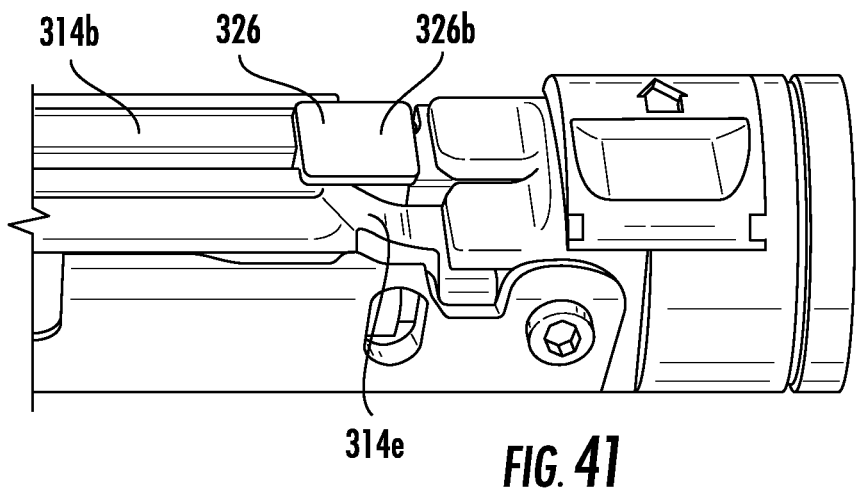
Figure 42:
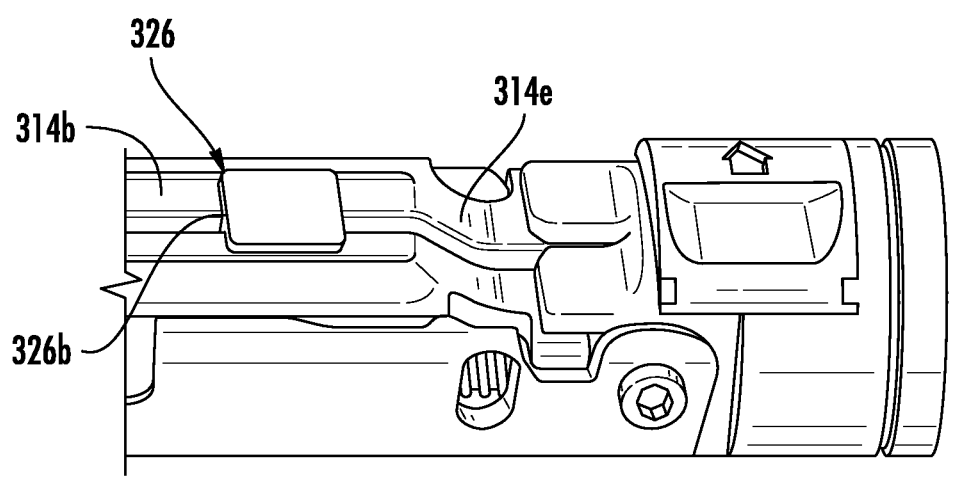

With reference to FIGS. 38, 41, and 42, the drive beam 326 of the cartridge assembly 320 is configured to translate longitudinally through the end effector 300 to approximate/ unapproximate the anvil and cartridge assemblies 310, 320 such as by pivoting the cartridge assembly 320 relative to the anvil assembly 310. While the drive beam 326 moves longitudinally through the end effector 300, the upper flange 326b of the drive beam 326 is configured to slide along the ramp 314e and the knife slide surface 314b of the anvil plate 314, and the lower flange 326b is configured to slide through the lower knife passage 322c of the cartridge body 322. The vertical member 326a further supports a knife 326e.

With continued reference to FIGS. 31, 32 and 38-40, the reload 330 of the end effector 300 includes a cartridge body 332 having a tissue contact surface 332a. The tissue contact surface 332a defines longitudinally extending rows of fastener retention slots 332b that support rows of fasteners 334 therein that correspond to rows of the fastener forming pockets (not shown) of the anvil assembly 310. Each row of fasteners 334 may include different sized fasteners 334 that may be arranged in ascending and/or descending order. The cartridge body 332 further includes tabs 332c that are received in the tab slots 322a of the support body 322 (e.g., snap-fit). The reload 330 further defines a longitudinally extending knife slot 332d that extends through the tissue contact surface 332a and is configured to receive the knife 326e of the drive beam 326 therethrough. The reload 330 further supports an actuation sled 336 that is engagable with the drive beam 326 and advanceable along the cartridge body 332 to engage pushers 338 that are supported within the cartridge body 332. The pushers 338 are positioned to support the fasteners 334 and vertically advance through the fastener retention slots 332b to eject the fasteners 334 therefrom for formation against the fastener forming pockets of the anvil assembly 310 as the actuation sled 336 engages the pushers 338.

In use, actuation of the actuation pad 108 causes rotation of one or more of the rotatable drive shafts 106 (e.g., clockwise and/or counterclockwise) of surgical device 100 via the one or more motors 103a disposed within surgical device 100.

Figure 43:
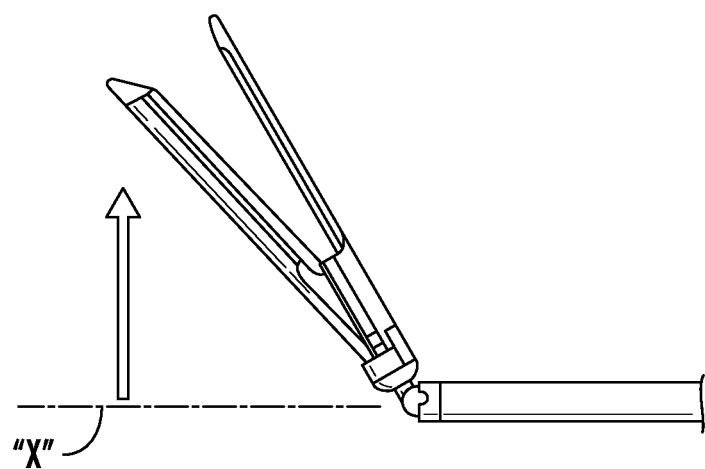
FIGS. 43 and 44 are side, perspective views illustrating the end effector of the electromechanical surgical system of FIG. 1 in articulated positions relative to the adapter assembly of FIG. 3.
Figure 44:
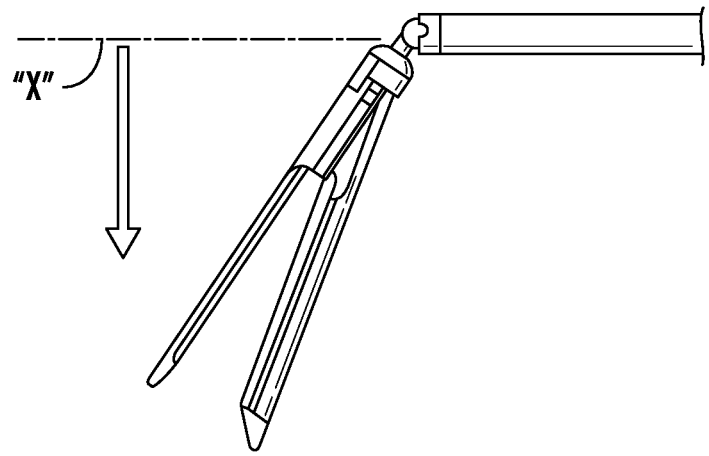

For instance, once the end effector 300 is coupled to the coupling member 206, the actuation pad 108 can be actuated to rotate one or both of the rotatable drive shafts 106a, 106c to articulate the end effector 300 and coupling member 206 relative to the shaft assembly 204. Rotation of the rotatable drive shaft 106c of the surgical device 100 causes a corresponding rotation of the first worm gear drive assembly 226 and rotation of the rotatable drive shaft 106a of the surgical device 100 causes a corresponding rotation of the second worm gear drive assembly 227. Rotation of the first and/or second worm gear drive assemblies 226, 227 causes respective first and/or second cable gear assemblies 224, 225 to draw/retract/tighten one or more of the cables 240 in one direction while letting out/releasing one or more of the cables 240 in an opposite direction so that the ferrules 240y of the respective cables 240 correspondingly draw/retract/ tighten and/or let out/release the coupling member 206 so as to articulate (e.g., pitch and/or yaw) the coupling member 206 and end effector 300 relative to the shaft assembly 204 and the longitudinal axis "X" (see FIGS. 43 and 44, for example). For a more detailed description of a similar translation of cables, reference can be made to U.S. Patent Application Publication No. 2015/0297199, the entire content of which is incorporated by reference herein.

Figure 10A:
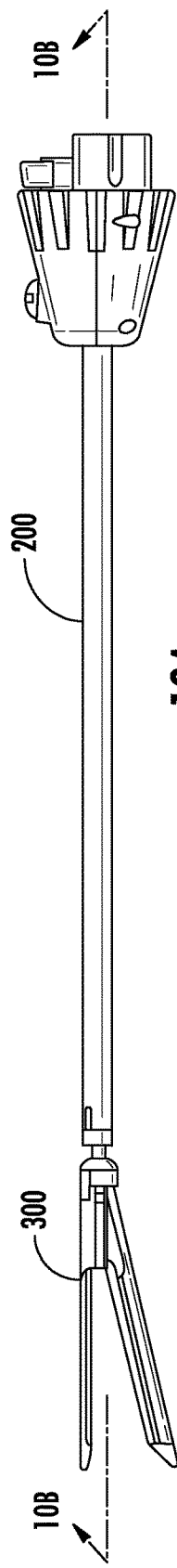
FIG. 10A is a plan view of the adapter assembly and end effector shown in FIG. 2 with the end effector disposed in an unarticulated and unclamped position.
Figure 10B:
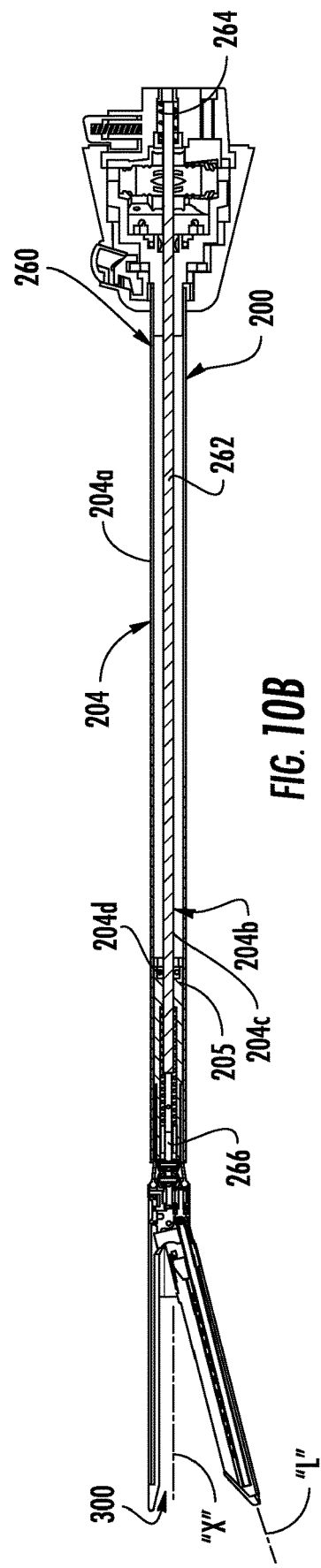
FIG. 10B is a cross-sectional view of the adapter assembly and end effector shown in FIG. 10A as taken along section line 10B-10B of FIG. 10A.
Figure 40:
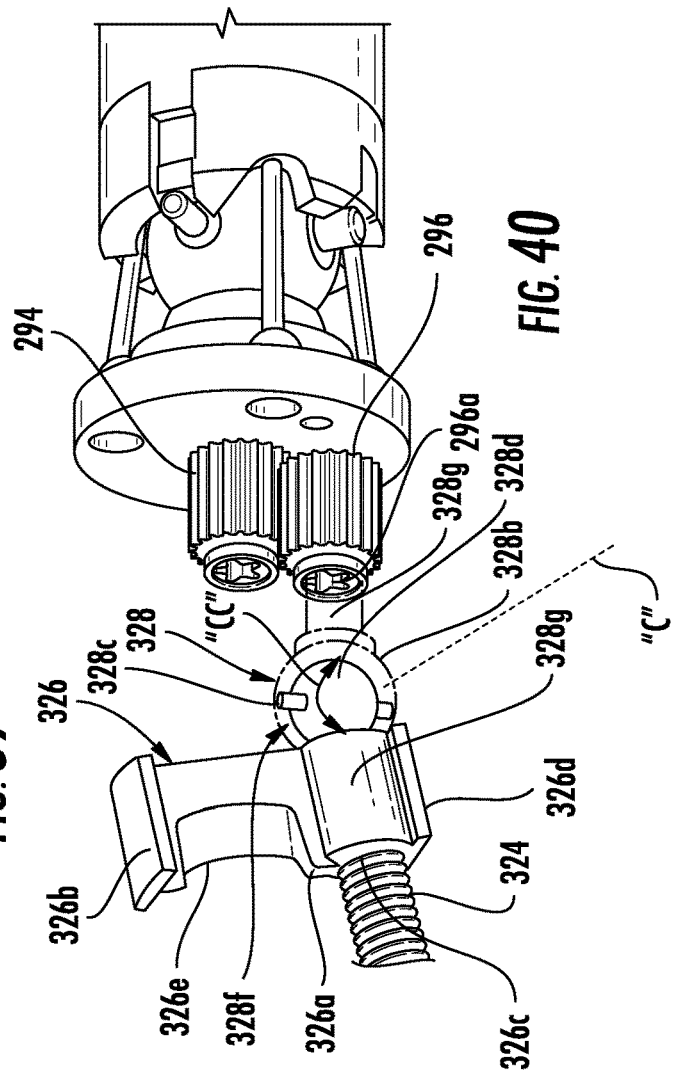

To clamp and fire the end effector 300, the actuation pad 108 of surgical device 100 is actuated to rotate the rotatable drive shaft 106b via the one or more motors 103a (see FIG. 1) within handle housing 102, and to effectuate rotation of the drive shaft 262 of the firing assembly 260 about the longitudinal axis "X" of the adapter assembly 200. Rotation of the drive shaft 262 of the firing assembly 260 rotates the joint assembly 266 of the firing assembly 260 so that the drive pin 280g of the second joint 280 of the joint assembly 266 causes rotation of the input coupler 294 of the coupling member 206 within the coupling member 206 (see FIG. 29). With reference to FIG. 40, rotation of the input coupler 294 causes the output coupler 296 of the coupling member 206 to rotate the drive joint 328 of the lead screw 324 so that the lead screw 324 rotates about its axis "L" (FIG. 10B).

With reference to FIGS. 38 and 39, rotation of the lead screw 324 of the cartridge assembly 320 enables the drive beam 326 of the cartridge assembly 320 to axially advance along the lead screw 324 by virtue of a threaded engagement between the lead screw 324 and the drive beam 326. As the drive beam 326 advances in response to rotation of the lead screw 324, the drive beam 326 slides along the ramp 314e of the anvil plate 314 until the drive beam 326 approximates or clamps the anvil and cartridge assemblies 310, 320 together (e.g., to clamp tissue between the anvil and cartridge assemblies 310, 320 for fastening). Continued distal advancement of the drive beam 326 causes the drive beam 326 to engage the actuation sled 336 of the reload 330 and advance through the longitudinal knife slot 332d (FIG. 32) of the reload 330 while maintaining the anvil and cartridge assemblies 310, 320 in approximation. Distal advancement of the drive beam 326 advances the actuation sled 336 into engagement with the pushers 338 of the reload 330 to fire the fasteners 334 from the fastener retention slots 332b of the reload 330 for forming against the corresponding fastener forming pockets (not shown) defined within the anvil plate 314 of the anvil assembly 310.

Reverse rotation of the lead screw 334 causes the drive beam 326 to retract so that the anvil and cartridge assemblies 310, 320 unapproximate to reset the end effector 300, whereby the reload 330 can be replaced so that the end effector 300 can then be re-fired as needed or desired.

As can be appreciated, securement of any of the components of the presently disclosed devices can be effectuated using known fastening techniques such welding, crimping, gluing, etc.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 45:
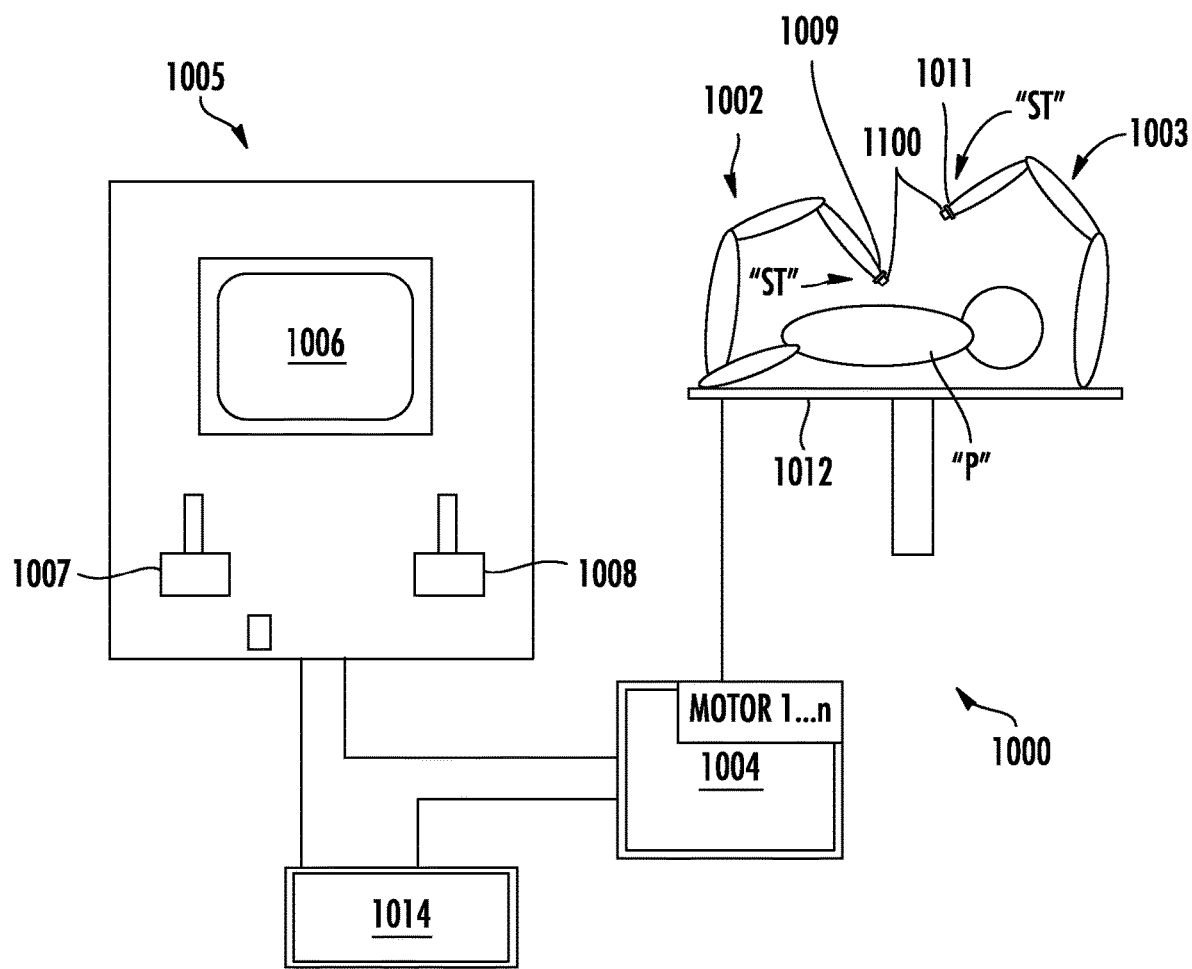
FIG. 45 is a schematic illustration of a medical work station and operating console in accordance with the present disclosure.

Referring also to FIG. 45, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members) in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A surgical system, such as the presently disclosed surgical system, may also be attached to the additional robot arm. The medical work station 1000 may include a database 1014 coupled with the control device 1004. In some embodiments, pre-operative data from patient/living being "P" and/or anatomical atlases may be stored in the database 1014. For a more detailed description of exemplary medical work stations and/or components thereof, reference may be made to U.S. Patent Application Publication No. 2012/0116416, filed on Nov. 3, 2011, entitled "Medical Workstation" and PCT Application Publication No. WO2016/025132, filed on Jul. 21, 2015, entitled "Robotically Controlling Mechanical Advantage Gripping, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system comprising:
an end effector including a staple cartridge assembly and an anvil assembly, the end effector further including a coupling ring and a slide member, the slide member defining a locking channel;
a surgical device configured to operate the end effector; and
an adapter assembly for selectively interconnecting the end effector and the surgical device, the adapter assembly defining a longitudinal axis and including:
at least one cable;
a coupling member secured to the at least one cable and selectively connectable to the end effector, the coupling member including a pin receivable within the locking channel of the slide member to selectively lock the coupling member of the adapter assembly within the coupling ring of the end effector; and
a firing assembly coupled to the coupling member and having a universal joint, the universal joint configured to facilitate articulation of the end effector relative to the longitudinal axis and rotatable to eject staples from the staple cartridge assembly.

2. The surgical system of claim 1, wherein the at least one cable includes a plurality of cables movable to articulate the coupling member in conjunction with corresponding movement of the universal joint.

3. The surgical system of claim 1, wherein the coupling member includes an input coupler and the firing assembly includes a drive pin, the input coupler rotatably receiving the drive pin therein.

4. The surgical system of claim 3, wherein the coupling member further includes an output coupler configured to rotate in response to rotation of the input coupler.

5. The surgical system of claim 4, wherein the end effector includes an input shaft rotatably coupled to the output coupler of the coupling member, the output coupler configured to rotate the input shaft to effectuate an approximation of the staple cartridge assembly and the anvil assembly and ejection of staples from the staple cartridge assembly.

6. The surgical system of claim 1, wherein the slide member is movable between open and closed positions relative to the coupling ring.

7. The surgical system of claim 6, wherein the slide member is spring biased toward the closed position.

8. The surgical system of claim 1, wherein the at least one cable includes a spherical ferrule that couples the at least one cable to the coupling member, the coupling member pivotable about the spherical ferrule.

* * * * *